US012662523B2

(12) United States Patent
Quan

(10) Patent No.: US 12,662,523 B2
(45) Date of Patent: Jun. 23, 2026

(54) PHARMACEUTICAL FORMULATIONS CONTAINING CD80 EXTRACELLULAR DOMAIN-FC FUSION PROTEINS

(71) Applicant: FIVE PRIME THERAPEUTICS, INC., Thousand Oaks, CA (US)

(72) Inventor: Yong Quan, Dublin, CA (US)

(73) Assignee: FIVE PRIME THERAPEUTICS, INC., Thousand Oaks, CA (US)

( * ) Notice: Subject to any disclaimer, the term of this patent is extended or adjusted under 35 U.S.C. 154(b) by 1199 days.

(21) Appl. No.: 17/608,546

(22) PCT Filed: May 1, 2020

(86) PCT No.: PCT/US2020/030946
§ 371 (c)(1),
(2) Date: Nov. 3, 2021

(87) PCT Pub. No.: WO2020/227062
PCT Pub. Date: Nov. 12, 2020

(65) Prior Publication Data
US 2022/0227834 A1     Jul. 21, 2022

Related U.S. Application Data

(60) Provisional application No. 62/842,722, filed on May 3, 2019.

(51) Int. Cl.
| | |
|---|---|
| *A61K 39/395* | (2006.01) |
| *A01K 67/0271* | (2024.01) |
| *A61K 9/00* | (2006.01) |
| *A61K 47/26* | (2006.01) |
| *A61P 35/00* | (2006.01) |
| *C07K 14/705* | (2006.01) |
| *A61K 38/00* | (2006.01) |

(52) U.S. Cl.
CPC .... *C07K 14/70532* (2013.01); *A01K 67/0271* (2013.01); *A61K 9/0019* (2013.01); *A61K 47/26* (2013.01); *A61P 35/00* (2018.01); *A01K 2227/105* (2013.01); *A01K 2267/0331* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 5,580,756 | A | 12/1996 | Linsley et al. |
| 6,071,716 | A | 6/2000 | Freeman et al. |
| 6,130,316 | A | 10/2000 | Freeman et al. |
| 6,218,510 | B1 | 4/2001 | Sharpe et al. |
| 6,294,660 | B1 | 9/2001 | Sharpe et al. |
| 6,319,709 | B1 | 11/2001 | Ostrand-Rosenberg et al. |
| 6,451,305 | B1 | 9/2002 | Bosiotis et al. |
| 6,491,925 | B2 | 12/2002 | Selvaraj et al. |
| 6,641,809 | B1 | 11/2003 | Linsley et al. |
| 6,653,444 | B1 | 11/2003 | Freeman et al. |
| 6,824,779 | B1 | 11/2004 | Freeman et al. |
| 6,887,471 | B1 | 5/2005 | Linsley et al. |
| 7,011,833 | B1 | 3/2006 | Sturmhoefel et al. |
| 7,064,111 | B1 | 6/2006 | Todo et al. |
| 7,070,776 | B1 | 7/2006 | Linsley et al. |
| 7,183,376 | B2 | 2/2007 | Punnonen et al. |
| 7,229,628 | B1 | 6/2007 | Allison et al. |
| 7,311,910 | B2 | 12/2007 | Linsley et al. |
| 7,619,078 | B2 | 11/2009 | Sharpe et al. |
| 7,678,890 | B2 | 3/2010 | Bosch |
| 7,749,718 | B2 | 7/2010 | Chirica et al. |
| 7,968,680 | B2 | 6/2011 | Green et al. |
| 8,114,845 | B2 | 2/2012 | Langermann et al. |
| 8,268,788 | B2 | 9/2012 | Epstein et al. |
| 8,956,619 | B2 | 2/2015 | Ostrand-Rosenberg |
| 8,969,526 | B2 | 3/2015 | Baehner et al. |
| 9,220,728 | B2 | 12/2015 | Sadelain et al. |
| 9,308,236 | B2 | 4/2016 | Miller et al. |
| 9,567,642 | B2 | 2/2017 | Feldser et al. |
| 9,650,429 | B2 | 5/2017 | Ostrand-Rosenberg et al. |
| 9,834,604 | B2 | 12/2017 | Zhu et al. |
| 9,879,046 | B2 | 1/2018 | Miller et al. |
| 10,273,281 | B2 | 4/2019 | Brennan et al. |
| 11,814,431 | B2 * | 11/2023 | Kaplan ............... C07K 16/2818 |
| 2004/0236091 | A1 | 11/2004 | Chicz et al. |
| 2006/0088523 | A1 * | 4/2006 | Andya ................... A61K 47/26 |
| | | | 424/133.1 |
| 2009/0041790 | A1 | 2/2009 | Rnak et al. |

(Continued)

FOREIGN PATENT DOCUMENTS

| | | | |
|---|---|---|---|
| EP | 2 662 383 A1 | 11/2013 | |
| EP | 2 856 876 B1 | 1/2018 | |

(Continued)

OTHER PUBLICATIONS

Alegre, M.-L., et al., "T-cell regulation by CD28 and CTLA-4," Nature Reviews Immunology 1:220-228, Macmillan Magazines Ltd., England (2001).
"Body Weight Information for C57BL/6J (000664)," Jackson Laboratory (JAX), available at http://www.jax.org/jax-mice-and-srvices/strain-datasheet-pages/body-eight-chart-000664 (Aug. 6, 2017), 2 pages.
Barbee, S., et al., "FPT155, a novel therapeutic CD 80-Fc fion protein, with potent anti-tumor activity in preclinical models," presented at 2017 AACR-EORTC International Conference on Molecular Targets and Cancer Therapeutics, Oct. 30, 2017, 1 page, California, United States.
Bhatia, S., et al., "Dynamic Equilibrium of B7-1 Dimers and Monomers Differentially Affects Immunological Synapse Formation and T Cell Activation in Response to TCR/CD28 Stimulation," The Journal of Immunology 184(4):1821-1828, The American Association of Immunologists, Inc., United States (2010).

(Continued)

*Primary Examiner* — Yunsoo Kim
(74) *Attorney, Agent, or Firm* — Melissa E. Karabinis

(57)     ABSTRACT

The present disclosure provides pharmaceutical compositions comprising CD80 extracellular domain (ECD)-fragment crystallizable (Fc) fusion molecules. The present disclosure also provides methods for treating solid tumors by administering such pharmaceutical compositions.

16 Claims, 11 Drawing Sheets
Specification includes a Sequence Listing.

(56)                    References Cited

U.S. PATENT DOCUMENTS

2011/0044953 A1    2/2011   Allison et al.
2011/0059078 A1    3/2011   Coyle et al.
2011/0223188 A1    9/2011   Langermann
2013/0017199 A1    1/2013   Langermann
2013/0149305 A1    6/2013   Ostrand-Rosenberg et al.
2014/0377253 A1   12/2014   Harding et al.
2016/0024179 A1    1/2016   Warner et al.
2016/0251437 A1    9/2016   Dong et al.
2017/0044268 A1    2/2017   Gurney et al.
2017/0145071 A1    5/2017   Brennan et al.
2017/0226181 A1    8/2017   Ostrand-Rosenberg et al.
2017/0274073 A1    9/2017   Grogan et al.
2017/0320959 A1   11/2017   Swanson et al.
2018/0044400 A1    2/2018   Kaempfer et al.
2018/0117145 A1    5/2018   Selvaraj et al.
2018/0244749 A1    8/2018   Swanson et al.
2019/0194288 A1    6/2019   Brennan et al.

FOREIGN PATENT DOCUMENTS

EP          3 330 290 A1     6/2018
EP          3 348 571 A1     7/2018
JP          2011514150 A     5/2011
WO          1997/47732 A2   12/1997
WO          1998/058965 A1  12/1998
WO          2003/039486 A2   5/2003
WO          2004/029197 A2   4/2004
WO          2008/037080 A1   4/2008
WO          2008/119071 A1  10/2008
WO          2008/121821 A1  10/2008
WO          2009/089149 A1   7/2009
WO          2013/019906 A1   2/2013
WO          2014/151006 A2   9/2014
WO          2015/200119 A1  12/2015
WO          2016/007235 A1   1/2016
WO          2016/161239 A1  10/2016
WO          2016/168771 A2  10/2016
WO          2016/174200 A1  11/2016
WO          2017/019846 A1   2/2017
WO          2017/042816 A1   3/2017
WO          2017/048878 A1   3/2017
WO          2017/079117 A1   5/2017
WO          2017/103291 A1   6/2017
WO          2017/144681 A1   8/2017
WO          2017/149150 A1   9/2017
WO          2017/151818 A2   9/2017
WO          2017/181152 A2  10/2017
WO          2017/201210 A1  11/2017
WO          2017/201352 A1  11/2017
WO          2018/064190 A1   4/2018
WO          2018/075978 A1   4/2018
WO          2018/201014 A1  11/2018
WO          2019/055902 A1   3/2019
WO          2020/047087 A1   3/2020
WO          2020/172482 A1   8/2020
WO          2020/227062 A1  11/2020

OTHER PUBLICATIONS

Bruggemann, C., et al., "Predictive value of PD-L1 based on mRNA level in the treatment of stage IV melanoma with Ipilimumab," Journal of Cancer Research and Clinical Oncology 143(10):1977-1984, Springer International, Germany (Oct. 2017).

Collins, M., et al., "The B7 family of immune-regulatory ligands," Genome Biology 6(6):223, BioMed Central Ltd., England, 7 pages (2005).

Contardi, E., et al., "CTLA-4 is constitutively expressed on tumor cells and can trigger apoptosis upon ligand interaction," Int. J. Cancer 117:538-550, Wiley-Liss, Inc., United States (2005).

Czajkowsky, D. M. et al."Fc-fion proteins: new developments and future perspectives," EMBO Molecular Medicine, 4(10): 1015-1028, Wiley Online Library, United States (2012).

Dalal, S.P., et al., "Mutated CD80 may facilitate T-cell activation by inhibiting PDL1—PD1 suppression and by costimulating," Cancer Res 73(8 Suppl): Abstract 1264, in Proceedings of the 104th Annual Meeting of the American Association for Cancer Research, April 6-10, American Association for Cancer Research, United States (2013).

Del Val, I., et al., "Towards the implementation of quality by design to the production of therapeutic monoclonal antibodies with desired glycosylation patterns," Biotechnology Progress 26(6): 1505-1527, American Institute of Chemical Engineers, United States (Dec. 2010).

Eastwood, D., et al., "Monoclonal antibody TGN1412 trial failure explained by species differences in CD28 expression on CD4+ effector memory T-cells," British Journal of Pharmacology 161:512-526, The British Pharmacological Society, England (2010).

Felix, J., et al., "Ipilimumab reshapes T cell memory subsets in melanoma patients with clinical response," Oncoimmunology 5(7):e1136045, Taylor & Francis Group, England, 10 pages (Feb. 18, 2016).

Findlay, L., et al., "Improved in vitro methods to predict the in vivo toxicity in man of therapeutic monoclonal antibodies including TGN1412," Journal of Immunological Methods 352(1-2):1-12, Elsevier B.V., Netherlands (2010).

Freeman, G.J., et al., "B7, a new member of the Ig superfamily with unique expression on activated and neoplastic B cells," J. Immunol. 143:2714-22, American Association of Immunologists, United States (1989).

Girard, T., et al., "CD80 and CD86 IgC domains are important for quaternary structure, receptor binding and co-signaling function," Immunology Letters 161:65-75, Elsevier B.V., Netherlands (2014).

Gogishvili, T., et al., "Rapid Regulatory T-Cell Response Prevents Cytokine Storm in CD28 Superagonist Treated Mice," PLoS ONE 4(2) :e4643, Public Library of Science, United States, 9 pages (2009).

Greaves, P. and Gribben, J.G., "The role of B7 family molecules in hematologic malignancy," Blood 121(5):734-744, American Society of Hematology, United States (2013).

Guan, J., et al., "Programmed Death Ligand-1 (PD-L1) Expression in the Programmed Death Receptor-1 (PD-1)/PD-L1 blockade: A Key Player Against Vario Cancers," Archives of Pathology & Laboratory Medicine 141(6):851-861, College of American Pathologists (Jun. 2017).

Haile, S.T et al. "A Soluble Form of CD80 Enhances Antitumor Immunity by Neutralizing Programmed Death Ligand-1 and Simultaneoly Providing Costimulation," Cancer Immunology Research, 2(7): 610-615, American Association of Cancer Research, United States (2014).

Horn, L.A., "Soluble CD80 Protein Delays Tumor Growth and Promotes TumorInfiltrating Lymphocytes," Cancer Immunology Research, 6(1): 59-68, (2018).

Hünig, T., "The storm has cleared: lessons from the CD28 superagonist TGN1412 trial," Nature Reviews Immunology 12:317-318, Macmillan Publishers Limited, England (2012).

Hunter, K.A., et al., "PD-L1 Testing in Guiding Patient Selection for PD-1/PD-L1 Inhibitor Therapy in Lung Cancer," Molecular Diagnosis and Therapy 22(1):1-10, Springer, Germany (Feb. 2018).

International Preliminary Report on Patentability for Application No. PCT/2016/059838, International Bureau of WIPO, Switzerland, mailed on May 8, 2018, 11 pages.

International Preliminary Report on Patentability International Application No. PCT/2018/029897, International Bureau of WIPO, Switzerland, mailed on Oct. 29, 2019, 7 pages.

International Search Report and Written Opinion for International Application No. PCT/2019/048560, European Patent Office, Netherlands, mailed Dec. 20, 2019, 21 pages.

International Search Report and Written opinion for International Application No. PCT/2020/019135, European Patent Office, Netherlands, mailed Aug. 19, 2020, 18 pages.

International Search Report and Written opinion for International Application No. PCT/2020/028715, International Search Authority, United States, mailed Jul. 17, 2020, 13 pages.

(56) References Cited

OTHER PUBLICATIONS

International Search Report and Written Opinion for International Application No. PCT/2020/030946, European Patent Office, Netherlands, mailed Sep. 1, 2020, 21 pages.

Jones, S., et al., "Lentiviral Vector Design for Optimal T Cell Receptor Gene Expression in the Transduction of Peripheral Blood Lymphocytes and Tumor-Infiltrating Lymphocytes," Human Gene Therapy 20(6):630-640, Mary Ann Liebert, United States (2009).

Kakoulidou, M., et al., "Human Soluble CD80 is Generated by Alternative Splicing, and Recombinant Soluble CD80 Binds to CD28 and CD 152 Influencing T-cell Activation," Scandinavian Journal of Immunology 66:529-537, Blackwell Publishing Ltd., England (2007).

Kaneko, Y., et al., "Anti-Inflammatory Activity of Immunoglobulin G Result from Fc Sialylation," Science 313:670-673, American Association for the Advancement of Science, United States (2006).

Klebanoff, C.A., et al., "Central memory self/tumor-reactive CD8+ T cells confer superior antitumor immunity compared with effector memory T cells," Proc Natl Acad Sci A 102(27):9571-9576, National Academy of Sciences, United States (2005).

Lechner, M.G., et al., "Chemokines, costimulatory molecules and fion proteins for the immunotherapy of solid tumors," Immunotherapy 3(11):1317-1340, Future Medicine, England (2011).

Lechner, M.G., et al., "Immunogenicity of murine solid tumor models as a defining feature of in vivo behavior and response to immunotherapy," J. Immunother. 36(9):477-489, Wolters Kluwer, United States (2013).

Linsley, P.S., et al., "Binding of the B Cell Activation Antigen B7 to CD28 Costimulates T Cell Proliferation and Interleukin 2 mRNA Accumulation," J. Exp. Med. 173:721-730, Rockefeller University Press, United States (Mar. 1991).

Linsley, et al., Human B7-1 (CD80) and B7-2 (CD86) Bind with Similar Avidities but Distinct Kinetics to CD28 and CTLA-4 Receptors, Immunity, vol. 1, 793-801, (1994).

Liu, A., et al., "Combination B7-Fc Fion Protein Treatment and Treg Cell Depletion Therapy," Clinical Cancer Research 11(23):8492-8502, American Association for Cancer Research, United States (2005).

Liu, L., "Antibody Glycosylation and Its Impact on the Pharmacokinetics and Pharmacodynamics of Monoclonal Antibodies and Fc-Fion Proteins," Journal of Pharmaceutical Sciences 104: 1866-1884, Elsevier, Netherlands (Apr. 2015).

Mahnke, Y.D., et al., "The who's who of T-cell differentiation: Human memory Tcell subsets," Eur J Immunol. 43(11):2797-2809, Wiley-VCH Verlag GmbH & Co. KGaA, Germany (2013).

Millward, M., et al., "FPT155001: A phase Ia/Ib study of FPT155 (CD80FC) in patients with advanced solid tumor," Journal of Clinical Oncology, 37(8): 2019 Ascositc Clinical Immuo-Oncology Symposium, (2019).

Oganesyan, V., et al., "Structural characterization of a human Fc fragment engineered for lack of effector functions," Acta Cryst. D64:700-04, International Union of Crystallography, Singapore (2008).

Ostrand-Rosenberg, S. et al., "Novel strategies for inhibiting PD-1 pathwaymediated immune suppression while simultaneoly delivering activating signals to tumor-reactive T cells," Cancer Immunology, Immunotherapy, 64(10): 1287-1293, Springer Link, Germany (2015).

Ostrand-Rosenberg, S., et al., "The programmed death-1 immune-suppressive pathway: barrier to antitumor immunity," The Journal of Immunology 193(8):3835-3841, The American Association of Immunologists, Inc., United States (2014).

Park, H-M., et al., "CD4 T-cells transduced with CD80 and 4-1BBL mRNA induce long-term CD8 T-cell responses resulting in potent antitumor effects," Vaccine 32:6919-6926, Elsevier Ltd., England (2014).

Paz-Ares, L., et al., "CheckMate 227: A Randomized, open-label phase 3 trial of nivolumab, nivolumab pl ipilimumab, or nivolumab pl chemotherapy vers chemotherapy in chemotherapy-naïve patients with advanced non-small cell lung cancer (NSCLC)", Annals of Oncology 28(2):ii50-ii51, Elsevier, Netherlands (Apr. 2017).

Peach, R.J., et al., "Both extracellular immunoglobin-like domains of CD80 contain residues critical for binding T cell surface receptors CTLA-4 and CD28," The Journal of Biological Chemistry 270(36):21181-21187, The American Society for Biochemistry and Molecular Biology, Inc., United States (1995).

Pützer, B.M., et al., "Interleukin 12 and B7-1 costimulatory molecule expressed by an adenovir vector act synergistically to facilitate tumor regression," Proc. Natl. Acad. Sci. A 94:10889-10894, The National Academy of Sciences, United States (1997).

R&D Systems, "Recombinant Human B7-1/CD80 Fc Chimera," Catalog No. 10107-B1, Revised Apr. 10, 2019, 2 pages.

Rajpal, A., et al., "Introduction: Antibody Structure and Function," Therapeutic FcFion Proteins 1(1):1-43, Wiley-VCH Verlag GmbH, Germany (2014).

Runyon, K., et al., "The combination of chemotherapy and systemic immunotherapy with soluble B7-immunoglobulin G leads to cure of murine leukemia and lymphoma and demonstration of tumor-specific memory responses," Blood 97:2420-2426, The American Society of Hematology, United States (2001).

Sallusto, F., "Central memory and Effector Memory T Cell Subsets; Function, Generation, and Maintenance," Annual Review of Immunology, 22(1): 745-763, Annual Reviews, United States (2004).

Sansom, D.M., "CD28, CTLA-4 and their ligands: who does what and to whom?" Immunology 101:169-177, Blackwell Science Ltd., England (2000).

Sola, Ricardo J., "Giycosylation of Therapeutics Proteins: An Effective Strategy to Optimize Efficacy," Biodrugs, 24(1): 9-21, Springer, United States (2010).

Sturmhoefel, K., et al., "Potent Activity of Soluble B7-IgG Fion Proteins in Therapy of Established Tumors and as Vaccine Adjuvant," Cancer Research 59:4964- 4972, American Association for Cancer Research, United States (1999).

Vessillier, S., et al., "Cytokine release assays for the prediction of therapeutic mAb safety in first-in man trials—Whole blood cytokine release assays are poorly predictive for TGN1412 cytokine storm," Journal of Immunological Methods 424:43-52, Elsevier B.V., Netherlands (May 7, 2015).

Waight, J.D., et al., "Selective Fc [gamma] R Co-engagement on APCs Modulates the Activity of Therapeutic Antibodies Targeting T cell Antigens," Cancer Cell 33(6):1033-1047, Cell Press, Netherlands (Jun. 2018).

Walker, L.S.K. and Sansom, D.M., "The emerging role of CTLA4 as a cellextrinsic regulator of T cell responses," Nature Reviews Immunology 11:852-863, Macmillan Publishers Limited, England (2011).

Weber, J.S., et al., "Ipilimumab increases activated T cells and enhances humoral immunity in patients with advanced melanoma," J Immunother. 35(1):89-97 (2012).

Yamaguchi, N., et al., "Induction of Tumor Regression by Administration of B7-Ig Fion Proteins: Mediation by Type 2 CD8+ T Cells and Dependence on IL-4 Production," The Journal of Immunology 172:1347-1354, The American Association of Immunologists, Inc., United States (2004).

Yao, S., et al., "Advances in targeting cell surface signaling molecules for immune modulation," Nature Reviews Drug Discovery 12:130-146, Macmillan Publishers Limited, England (2013).

Zhang, L., et al., "Programmed cell death ligand 1 (PD-L1) expression on gastric cancer and its relationship with clinicopathologic factors," Int J. Clin Exp Pathol, 8(9):11084-11091, E-century Publishing Corp, United States (2015).

* cited by examiner 10 mg/mL hCD80-Fc in 20 mM L-histidine, 270 mM sucrose, 0.05% PS20 at pH 6.7

Tm1: 62.68
Tm2: 84.83

PHARMACEUTICAL FORMULATIONS CONTAINING CD80 EXTRACELLULAR DOMAIN-FC FUSION PROTEINS

CROSS-REFERENCE TO RELATED APPLICATIONS

This application is a 35 U.S.C. § 371 National Phase Application of International Application No. PCT/US2020/030946, filed May 1, 2020, which claims the benefit of U.S. Provisional Application No. 62/842,722, filed May 3, 2019, the content each of which is incorporated herein by reference in its entirety.

REFERENCE TO A SEQUENCE LISTING SUBMITTED ELECTRONICALLY VIA EFS-WEB

The content of the electronically submitted sequence listing (Name: 3986_0200001_Seqlisting_ST25.txt; Size: 14,036 bytes; and Date of Creation: Aug. 19, 2021) is herein incorporated by reference in its entirety.

FIELD

Pharmaceutical compositions (formulations) comprising fusion proteins are provided. The fusion proteins comprise an CD80 (B7-1) extracellular domain (ECD) and an immunoglobulin fragment crystallizable (Fc) domain. Methods of using such formulations are also provided.

BACKGROUND

T-cell regulation involves the integration of multiple signaling pathways: signaling via the T-cell receptor (TCR) complex and through co-signaling receptors, both co-stimulatory and co-inhibitory. CD80 (cluster of differentiation 80, also known as B7, B7.1, B7-1) is a well-characterized co-signaling ligand. It is expressed on professional antigen-presenting cells (APCs) such as dendritic cells and activated macrophages. APCs present antigenic peptides to T-cells by displaying them in the context of major histocompatibility complex (MHC) molecules. Upon TCR recognition of peptide-MHC complexes, CD80 acts as a co-stimulatory ligand via interactions with its receptor, cluster of differentiation 28 (CD28), expressed on T-cells. In addition to signaling via CD28, CD80 also interacts with cytotoxic T-lymphocyte-associated antigen-4 (CTLA-4), a co-inhibitory molecule. CD80 interactions with CTLA-4 are central for dampening the T-cell response once activated T-cell responses are no longer needed. According to some reports, CD80 interacts with PD-L1. However, it is not clear whether this interaction takes place and if so, what is the biological significance. Together, co-stimulatory and co-inhibitory signals ensure both tolerance to self-antigens and the ability to mount an appropriate immune response to non-self antigens.

Although the immune system is often initially able to mount an effective immune response against tumor cells via TCR-dependent and -independent mechanisms, tumors can evade the immune response. Mechanisms by which this occurs include the upregulation of pathways that enforce peripheral tolerance to self-antigens (including CTLA-4 and PD-L1). Recent immuno-oncology approaches have focused on reprogramming the immune system to mount an effective immune response against tumors that have evaded the initial immune response. These approaches include the use of immune response. These approaches include the use of "checkpoint inhibitors." For example, blocking antibodies against both the programmed cell death protein (PD-1)/PD-L1 and CTLA-4 axes have been effective in anti-tumor immunity, including improved progression free survival (PFS) and overall survival (OS) in some patients. Although some patients with certain tumor types do achieve long term disease control with the use of blocking antibodies against the PD-1/PD-L1 or CTLA-4 axes, the majority of patients either do not respond or respond then subsequently relapse.

The CD80 signaling axis may provide additional opportunities for the treatment of cancer, and CD80 extracellular domain (ECD)-Fc fusion proteins are being developed for that purpose. Accordingly, there is a need for pharmaceutical compositions comprising CD80 ECD-Fc fusion proteins formulated for administration of such treatments.

SUMMARY

Provided herein are pharmaceutical compositions comprising CD80 extracellular domain (ECD)-fragment crystallizable (Fc) fusion molecules. In certain embodiments, a pharmaceutical composition comprises (i) CD80 ECD-Fc fusion molecules, (ii) histidine, and (iii) a sugar selected from the group consisting of sucrose and sorbitol, wherein the pH of the composition is about 5 to about 7.5.

In certain embodiments, a composition comprises no more than 10% of high molecular weight species (HMWS) of the fusion molecules after 4 weeks at 40° C.

In certain embodiments, a composition comprises about 1% to about 10% of HMWS of the fusion molecules after 4 weeks at 40° C.

In certain embodiments, a composition comprises no more than 2.5% of low molecule weight species (LMWS) of the CD80 ECD-Fc fusion molecules after 4 weeks at 40° C.

In certain embodiments, a composition comprises about 0.5% to about 2.5% of LMWS of the CD80 ECD-Fc fusion molecules after 4 weeks at 40° C.

In certain embodiments, a composition comprises about 1% to about 6% of HMWS of the fusion molecules after 4 weeks at 40° C.

In certain embodiments, a composition comprises about 1% to about 4% of HMWS of the fusion molecules after 4 weeks at 40° C.

In certain embodiments, a composition comprises about 0.5% to about 1.6% of LMWS of the CD80 ECD-Fc fusion molecules after 4 weeks at 40° C.

In certain embodiments, a composition comprises about 0.5% to about 1.5% of LMWS of the CD80 ECD-Fc fusion molecules after 4 weeks at 40° C.

In certain embodiments, the pH of the composition is about 5 to about 7.5. In certain embodiments, the composition has a pH of about 5.5 to about 7.0. In certain embodiments, the composition has a pH of about 6.4 to about 7.0. In certain embodiments, the composition has a pH of about 6.7.

In certain embodiments, the composition comprises histidine, optionally wherein the histidine is L-histidine. In certain embodiments, the concentration of the histidine (e.g., L-histidine) is about 15 to about 25 mM. In certain embodiments, the concentration of the histidine (e.g., L-histidine) is about 18 mM to about 22 mM. In certain embodiments, the concentration of the histidine (e.g., L-histidine) is about 20 mM.

In certain embodiments, the composition further comprises a sugar selected from the group consisting of sucrose and sorbitol. In certain embodiments, the sugar is sucrose. In certain embodiments, the sugar is sorbitol.

In certain embodiments, the concentration of the sugar is about 225 mM to about 300 mM. In certain embodiments, the concentration of the sugar is about 250 mM to about 290 mM. In certain embodiments, the concentration of the sugar is about 270 mM.

In certain embodiments, the concentration of the sugar is about 10 to about 15 times the concentration of the histidine, optionally wherein the concentration of the sugar is about 13.5 times the concentration of the buffer.

In certain embodiments, the composition further comprises a surfactant.

In certain embodiments, the surfactant is polysorbate, optionally wherein the polysorbate is polysorbate 20. In certain embodiments, the concentration of the surfactant is about 0.025% to about 0.075% weight/volume (w/v). In certain embodiments, the concentration of the surfactant is about 0.035% to about 0.065% weight/volume (w/v). In certain embodiments, the concentration of the surfactant is about 0.05% weight/volume (w/v).

In certain embodiments, the concentration of CD80 ECD-Fc fusion molecules is about 5 mg/ml to about 15 mg/ml. In certain embodiments, the concentration of the CD80 ECD-Fc fusion molecules is about 10 mg/ml.

In certain embodiments, the composition is a liquid.

In certain embodiments, the composition is for intravenous administration.

In certain embodiments, the composition comprises about 20 mM histidine, about 270 mM sucrose, about 10 mg/ml of the CD80 ECD-Fc fusion molecules, and about 0.05% polysorbate 20, wherein the pH is about 6.7.

In certain embodiments, the composition comprises a concentration of sugar that is about 13.5 times the concentration of histidine, about 10 mg/ml of the CD80 ECD-Fc fusion molecules, and about 0.05% polysorbate 20, wherein the pH is about 6.7.

In certain embodiments, the composition comprises about 20 mM histidine (e.g., L-histidine), about 270 mM sorbitol, about 10 mg/ml of the CD80 ECD-Fc fusion molecules, and about 0.05% polysorbate 20, wherein the pH is about 6.7.

In certain embodiments, the composition comprises a concentration of sorbitol that is about 13.5 times the concentration of histidine, about 10 mg/ml of the CD80 ECD-Fc fusion molecules, and about 0.05% polysorbate 20, wherein the pH is about 6.7.

In certain embodiments, the CD80 ECD-Fc fusion molecules comprise a human CD80 ECD and a human IgG1 Fc domain.

In certain embodiments, the composition comprises sialylated CD80 ECD-Fc fusion molecules.

In certain embodiments, the CD80 ECD-Fc fusion molecules comprise at least 15 moles of sialic acid (SA) per mole of fusion protein.

In certain embodiments, the CD80 ECD-Fc fusion molecules comprise 15-60 moles SA per mole of fusion protein. In certain embodiments, the CD80 ECD-Fc fusion molecules comprise 15-40 moles SA per mole of fusion protein. In certain embodiments, the CD80 ECD-Fc fusion molecules comprise 15-30 moles SA per mole of fusion protein. In certain embodiments, the CD80 ECD-Fc fusion molecules comprise 20-30 moles SA per mole of fusion protein.

In certain embodiments, the CD80 ECD-Fc fusion molecules comprise a human CD80 ECD comprising the amino acid sequence of SEQ ID NO:1.

In certain embodiments, the CD80 ECD-Fc fusion molecules comprise a human IgG1 Fc domain comprising the amino acid sequence of SEQ ID NO:4.

In certain embodiments, the CD80 ECD-Fc fusion molecules comprise the Fc domain of human IgG1 linked to the carboxy terminus of the ECD of human CD80.

In certain embodiments, the CD80 ECD-Fc fusion molecules comprise the amino acid sequence of SEQ ID NO:5.

In certain embodiments, the composition alone causes less release of interferon gamma or TNF alpha from T-cells in vitro than TGN1412 alone.

In certain embodiments, the composition alone is at least 1000-fold less potent at inducing interferon gamma or TNF alpha release compared to TGN1412 alone.

In certain embodiments, the composition is capable of at least 90% tumor growth inhibition in at least one mouse syngeneic cancer model over a period of at least one week, 10 days, two weeks, or three weeks following administration of a single dose of the composition at 0.3 to 0.6 mg/kg.

In certain embodiments, the mouse syngeneic cancer model is a CT26 tumor model.

In certain embodiments, a pharmaceutical composition consists of (i) sialylated CD80 ECD-Fc fusion molecules, (ii) about 20 mM L-histidine, (iii) about 270 mM sucrose, and (iv) about 0.05% weight/volume polysorbate 20, wherein the pH of the composition is about 6.7.

In certain embodiments, a pharmaceutical composition consists of sialylated CD80 ECD-Fc fusion molecules, (ii) about 20 mM L-histidine, (iii) about 270 mM sorbitol, and (iv) about 0.05% weight/volume polysorbate 20, wherein the pH of the composition is about 6.7.

In certain embodiments, provided herein is a syringe or vial comprising the pharmaceutical composition.

In certain embodiments, provided herein is a method of treating a solid tumor in a subject. In certain embodiments the method comprises administering to the subject a pharmaceutical composition provided herein. In certain embodiments, the subject is human.

In certain embodiments, the solid tumor is an advanced solid tumor.

In certain embodiments, the solid tumor is not a primary central nervous system tumor.

In certain embodiments, the solid tumor is a colorectal cancer, breast cancer, gastric cancer, non-small cell lung cancer, small cell lung cancer, melanoma, squamous cell carcinoma of the head and neck, ovarian cancer, pancreatic cancer, renal cell carcinoma, hepatocellular carcinoma, bladder cancer, or endometrial cancer.

In certain embodiments, the solid tumor is a renal cell carcinoma.

In certain embodiments, the solid tumor is melanoma.

In certain embodiments, the patient has not received prior therapy with a PD-1/PD-L1 antagonist.

In certain embodiments, the patient has received prior therapy with at least one PD-1/PD-L1 antagonist selected from a PD-L1 antagonist and a PD-1 antagonist. In certain embodiments, the at least one PD-1/PD-L1 antagonist is nivolumab, pembrolizumab, atezolizumab, durvalumab, or avelumab.

In certain embodiments, the at least one PD-1/PD-L1 antagonist was administered in an advanced or metastatic setting.

In certain embodiments, the patient has received prior therapy with at least one anti-angiogenic agent. In certain embodiments, the anti-angiogenic agent is sunitinib, sorafenib, pazopanib, axitinib, tivozanib, ramucirumab, or bevacizumab.

In certain embodiments, the anti-angiogenic agent was administered in an advanced or metastatic setting.

In certain embodiments, the patient has a BRAF mutation.

In certain embodiments, the patient has received prior therapy with at least one BRAF inhibitor.

In certain embodiments, the BRAF inhibitor is vemurafenib or dabrafenib.

In certain embodiments, the BRAF inhibitor was administered in an advanced or metastatic setting.

In certain embodiments, the solid tumor is recurrent or progressive after a therapy selected from surgery, chemotherapy, radiation therapy, and a combination thereof.

In certain embodiments, the pharmaceutical composition is administered intravenously.

DETAILED DESCRIPTION

Figure 1:
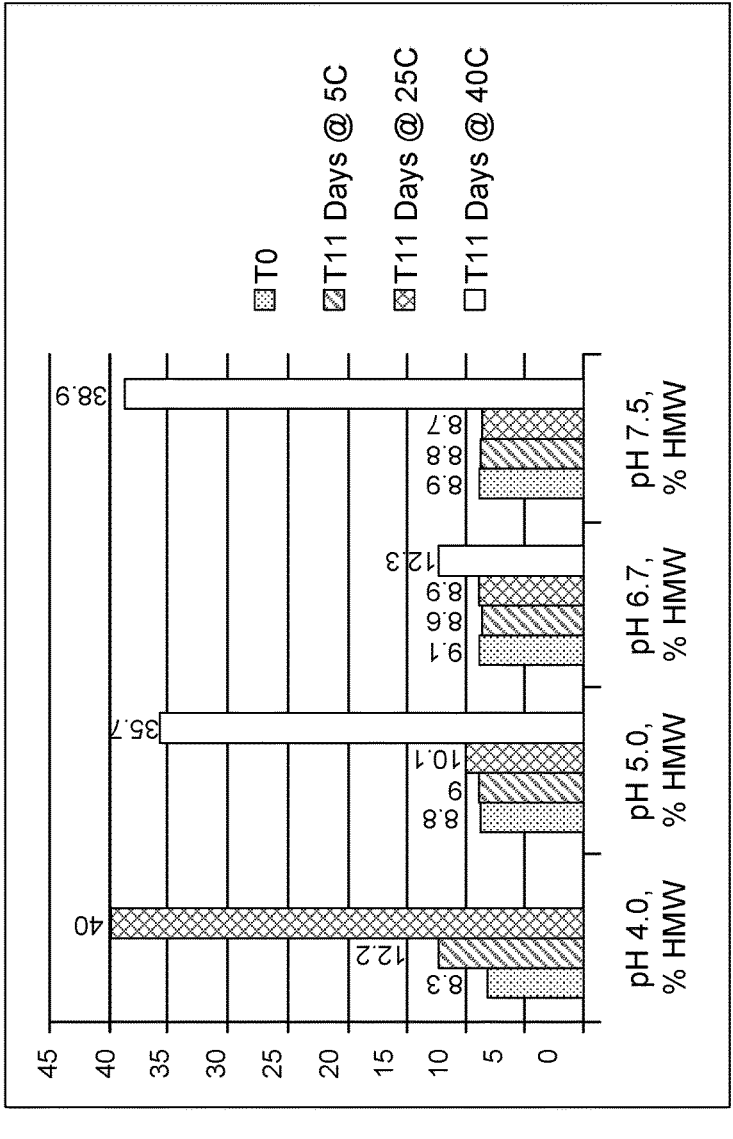
FIG. 1 shows the impact of buffer pH on aggregate formation as determined by Size Exclusion High Performance Liquid Chromatography (SE-HPLC). (See Example 3.)

Provided herein are pharmaceutical compositions comprising CD80 extracellular domain (ECD)-fragment crystallizable (Fc) fusion molecules. The pharmaceutical compositions can be stable e.g., under long-term storage conditions, through repeated freeze-thaw cycles (e.g., at least 5 cycles), and/or through agitation.

As provided herein, a pharmaceutical composition can comprise CD80 ECD-Fc fusion molecules (e.g., at a concentration of about 5 to about 15 mg/ml), histidine (e.g. L-histidine), a sugar (e.g., sucrose or sorbitol), and/or a surfactant (including but not limited to polysorbate, e.g., polysorbate 20 (PS20)).

In a particular embodiment, a liquid aqueous pharmaceutical composition containing 10 mg/mL of CD80 ECD-Fc fusion molecules (e.g., human CD80 ECD-human IgG1 fusion molecules as in SEQ ID NO:5) in 20 mM histidine (e.g., L-histidine), 270 mM sucrose, and 0.05% PS20 with a pH of 6.7 is provided herein. In another particular embodiment, a liquid aqueous pharmaceutical composition containing 10 mg/mL of CD80 ECD-Fc fusion molecules (e.g., human CD80 ECD-human IgG1 fusion molecules as in SEQ ID NO:5) in 20 mM histidine (e.g., L-histidine), 270 mM sorbitol, and 0.05% PS20 with a pH of 6.7 is provided herein.

The pharmaceutical compositions provided herein can be useful for treating conditions such as a solid tumor.

Terminology

A "fusion molecule" as used herein refers to a molecule composed of two or more different molecules that do not occur together in nature being covalently or noncovalently joined to form a new molecule. For example, fusion molecules may be comprised of a polypeptide and a polymer such as PEG, or of two different polypeptides. A "fusion protein" refers to a fusion molecule composed of two or more polypeptides that do not occur in a single molecule in nature.

A "CD80 extracellular domain" or "CD80 ECD" refers to an extracellular domain polypeptide of CD80, including natural and engineered variants thereof. A CD80 ECD can, for example, comprise, consist essentially of, or consist of the amino acid sequence set forth in SEQ ID NO:1 or 2. A "CD80 ECD fusion molecule" refers to a molecule comprising a CD80 ECD and a fusion partner. The fusion partner may be covalently attached, for example, to the N- or C-terminal of the CD80 ECD or at an internal location. A CD80 ECD fusion molecule can be a fusion protein comprising a CD80 ECD and another polypeptide that is not naturally associated with the CD80 ECD, such as an Fc domain. Such a CD80 ECD-Fc fusion molecule, for example, can comprise, consist essentially of, or consist of the amino acid sequence set forth in SEQ ID NO:4 or 5.

The terms "polypeptide," "peptide," and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present invention, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

The term "isolated" as used herein refers to a molecule that has been separated from at least some of the components with which it is typically found in nature. For example, a polypeptide is referred to as "isolated" when it is separated from at least some of the components of the cell in which it was produced. Where a polypeptide is secreted by a cell after expression, physically separating the supernatant containing the polypeptide from the cell that produced it is considered to be "isolating" the polypeptide. Similarly, a polynucleotide is referred to as "isolated" when it is not part of the larger polynucleotide (such as, for example, genomic DNA or mitochondrial DNA, in the case of a DNA polynucleotide) in which it is typically found in nature, or is separated from at least some of the components of the cell in which it was produced, e.g., in the case of an RNA polynucleotide. Thus, a DNA polynucleotide that is contained in a vector inside a host cell may be referred to as "isolated" so long as that polynucleotide is not found in that vector in nature.

As used herein, the term "host cell" can be any type of cell, e.g., a primary cell, a cell in culture, or a cell from a cell line. In specific embodiments, the term "host cell" refers to a cell transfected with a nucleic acid molecule and the progeny or potential progeny of such a cell. Progeny of such a cell may not be identical to the parent cell transfected with the nucleic acid molecule, e.g., due to mutations or environmental influences that may occur in succeeding generations or integration of the nucleic acid molecule into the host cell genome.

The term "pharmaceutical formulation" or "pharmaceutical composition" refers to a preparation which is in such form as to permit the biological activity of the active ingredient to be effective, and which contains no additional components which are unacceptably toxic to a subject to which the formulation would be administered. The formulation can be sterile.

The term "drug product" refers to a finished dosage form, e.g., a liquid formulation containing a drug substance, generally, but not necessarily, in association with one or more other ingredients.

The term "drug substance" refers to an active ingredient, e.g., CD80 ECD-Fc fusion molecules, that is intended to furnish pharmacological or biological activity or other direct effect in the diagnosis, cure, mitigation, treatment, or prevention of disease, but does not include intermediates used in the synthesis of such ingredient.

As used herein, "buffer" refers to a component in a solution that allows the solution to resist changes in pH. Buffers include, for example, acetate, citrate, succinate, and histidine.

A "stable" formulation is one in which the active ingredient (e.g., CD80 ECD-Fc fusion molecules) therein substantially retains its physical stability and/or chemical stability and/or biological activity upon storage. Stability can be measured at a selected condition (e.g., temperature) for a selected time period. Formulations provided herein can be stable at room temperature (about 25° C.) for at least 6 months and/or stable at about 2-8° C. for at least 1 year. Formulations provided herein can also be stable following freezing (e.g., to −70° C.) and thawing of the formulation, hereinafter referred to as a "freeze/thaw cycle." Formulations provided herein can also be stable after agitation.

The terms "administer", "administering", "administration", and the like, as used herein, refer to methods that may be used to enable delivery of a drug, e.g., CD80 ECD-Fc fusion molecules, to the desired site of biological action (e.g., intravenous administration). Administration techniques that can be employed with the agents and methods described herein are found in e.g., Goodman and Gilman, The Pharmacological Basis of Therapeutics, current edition, Pergamon; and Remington's, Pharmaceutical Sciences, current edition, Mack Publishing Co., Easton, Pa.

As used herein, the terms "subject" and "patient" are used interchangeably. The subject can be an animal. In some embodiments, the subject is a mammal such as a non-human animal (e.g., cow, pig, horse, cat, dog, rat, mouse, monkey or other primate, etc.). In some embodiments, the subject is a cynomolgus monkey. In some embodiments, the subject is a human.

The term "therapeutically effective amount" refers to an amount of a drug, e.g., CD80 ECD-Fc fusion molecules, effective to treat a disease or disorder in a subject. In the case of a solid tumor, the therapeutically effective amount of the drug can reduce the number of cancer cells; reduce the tumor size or burden; inhibit, to some extent, cancer cell infiltration into peripheral organs; inhibit, to some extent, tumor metastasis; inhibit, to some extent, tumor growth; relieve, to some extent, one or more of the symptoms associated with the cancer; and/or result in a favorable response such as increased progression-free survival (PFS), disease-free survival (DFS), overall survival (OS), complete response (CR), partial response (PR), or, in some cases, stable disease (SD), a decrease in progressive disease (PD), a reduced time to progression (TTP), or any combination thereof. To the extent the drug can prevent growth and/or kill existing cancer cells, it can be cytostatic and/or cytotoxic.

Terms such as "treating," "treatment," "treat," "alleviating," and "alleviate" refer to therapeutic measures that cure, slow down, lessen symptoms of, and/or halt progression of a pathologic condition or disorder. Thus, those in need of treatment include those already diagnosed with or suspected of having the disorder. In certain embodiments, a subject is successfully "treated" for cancer according to the methods of the present invention if the patient shows one or more of the following: a reduction in the number of or complete absence of cancer cells; a reduction in the tumor size; inhibition of or an absence of cancer cell infiltration into peripheral organs including, for example, the spread of cancer into soft tissue and bone; inhibition or an absence of tumor metastasis; inhibition or an absence of tumor growth; relief of one or more symptoms associated with the specific cancer; reduced morbidity and mortality; improvement in quality of life; reduction in tumorigenicity, tumorigenic frequency, or tumorigenic capacity, of a tumor; reduction in the number or frequency of cancer stem cells in a tumor; differentiation of tumorigenic cells to a non-tumorigenic state; increased progression-free survival (PFS), disease-free survival (DFS), overall survival (OS), complete response (CR), partial response (PR), stable disease (SD), a decrease in progressive disease (PD), a reduced time to progression (TTP), or any combination thereof.

The terms "cancer" and "cancerous" refer to or describe the physiological condition in mammals in which a population of cells are characterized by unregulated cell growth. Examples of cancer include, but are not limited to, colorectal cancer, breast cancer, gastric cancer, non-small cell lung cancer, melanoma, squamous cell carcinoma of the head and neck, ovarian cancer, pancreatic cancer, renal cell carcinoma, hepatocellular carcinoma, bladder cancer, and endometrial cancer. The cancer may be a primary tumor or may be advanced or metastatic cancer.

A "refractory" cancer is one that progresses even though an anti-tumor treatment, such as a chemotherapy, is administered to the cancer patient.

A "recurrent" cancer is one that has regrown, either at the initial site or at a distant site, after a response to initial therapy.

A "relapsed" patient is one who has signs or symptoms of cancer after remission. In certain embodiments, the patient has relapsed after adjuvant or neoadjuvant therapy.

As used in the present disclosure and claims, the singular forms "a," "an," and "the" include plural forms unless the context clearly dictates otherwise.

It is understood that wherever embodiments are described herein with the language "comprising," otherwise analogous embodiments described in terms of "consisting of" and/or "consisting essentially of" are also provided. In this disclosure, "comprises," "comprising," "containing" and "having" and the like can have the meaning ascribed to them in U.S.

patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited are not changed by the presence of more than that which is recited, but excludes prior art embodiments Unless specifically stated or obvious from context, as used herein, the term "or" is understood to be inclusive. The term "and/or" as used in a phrase such as "A and/or B" herein is intended to include both "A and B," "A or B," "A," and "B." Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

As used herein, the terms "about" and "approximately," when used to modify a numeric value or numeric range, indicate that deviations of up to 10% above and up to 10% below the value or range remain within the intended meaning of the recited value or range.

Any compositions or methods provided herein can be combined with one or more of any of the other compositions and methods provided herein.

Pharmaceutical Compositions Comprising CD80 ECD-Fc Fusion Molecules

Provided herein are pharmaceutical compositions (e.g., aqueous pharmaceutical compositions) comprising CD80 ECD-Fc fusion molecules (e.g., as discussed in Section 5.3 below).

In certain embodiments, a pharmaceutical composition provided herein is stable to multiple freeze-thaw cycles. A freeze-thaw cycle can comprise freezing the pharmaceutical composition (e.g., at a temperature of about −70° C.) and then thawing the pharmaceutical composition (e.g., at room temperature). The pharmaceutical composition can be stable through at least five freeze-thaw cycles. The freeze-thaw cycles (e.g., the at least five freeze-thaw cycles) can result in no detectable change in appearance, soluble aggregates, or subvisible particulate matter.

In certain embodiments, a pharmaceutical composition provided herein is stable through agitation. The agitation can comprise shaking (e.g. at about 300 rotations per minute on an orbital shaker) for about three days at room temperature. The agitation can result in no detectable change in appearance, soluble aggregates, charge variant profiles, or subvisible particulate matter.

In certain embodiments, a pharmaceutical composition provided herein is stable under long-term storage conditions. The long-term storage conditions can comprise storage at about 5° C. (e.g., about 2° C. to about 8° C.) for about 6 months or about 1 year. The long-term storage conditions can comprise storage at about 25° C. for about 6 months or about 1 year. The long-term storage conditions can comprise storage at about 40° C. for about 3 months, about 6 months or about 1 year.

In certain embodiments, a pharmaceutical composition provided herein is stable to multiple (e.g., at least five) freeze-thaw cycles, stable through agitation, and/or stable under long-term storage conditions.

In certain embodiments, a pharmaceutical composition provided herein is stable for about 1 year when stored at about −70° C. or when stored at about 2° C. to about 8° C.

In certain embodiments, the pharmaceutical composition can contain CD80 ECD-Fc fusion molecules (e.g., comprising the amino acid sequence of SEQ ID NO:5). In certain embodiments, the concentration of the CD80 ECD-Fc fusion molecules (e.g., comprising the amino acid sequence of SEQ ID NO:5) in the formulation is about 5 mg/ml to about 15 mg/ml. In certain embodiments, the concentration of the CD80 ECD-Fc fusion molecules (e.g., comprising the amino acid sequence of SEQ ID NO:5) in the pharmaceutical composition is about 10 mg/ml.

In certain embodiments, the concentration of the CD80 ECD-Fc fusion molecules (e.g., comprising the amino acid sequence of SEQ ID NO:5) in the formulation is 5 mg/ml to 15 mg/ml. In certain embodiments, the concentration of the CD80 ECD-Fc fusion molecules (e.g., comprising the amino acid sequence of SEQ ID NO:5) in the pharmaceutical composition is 10 mg/ml.

As provided herein, the pharmaceutical composition can contain a buffer. In certain embodiments, the buffer is histidine (e.g., L-histidine). In certain embodiments, the concentration of the histidine (e.g., L-histidine) is about 15 mM to about 25 mM. In certain embodiments, the concentration of the histidine (e.g., L-histidine) is about 18 mM to about 22 mM. In certain embodiments, the concentration of the histidine (e.g., L-histidine) is about 20 mM.

In certain embodiments, the concentration of the histidine (e.g., L-histidine) is 15 mM to 25 mM. In certain embodiments, the concentration of the histidine (e.g., L-histidine) is 18 mM to 22 mM. In certain embodiments, the concentration of the histidine (e.g., L-histidine) is 20 mM.

As provided herein, the pharmaceutical composition can contain an excipient, for example, a sugar such as sucrose or sorbitol. In some embodiments, the concentration of the sugar (e.g., sucrose or sorbitol) is about 225 mM to about 300 mM. In some embodiments, the concentration of the sugar (e.g., sucrose or sorbitol) is about 250 mM to about 290 mM. In some embodiments, the concentration of the sugar (e.g., sucrose or sorbitol) is about 270 mM.

In some embodiments, the concentration of the sugar (e.g., sucrose or sorbitol) is 225 mM to mM. In some embodiments, the concentration of the sugar (e.g., sucrose or sorbitol) is 250 mM to 290 mM. In some embodiments, the concentration of the sugar (e.g., sucrose or sorbitol) is 270 mM.

As provided herein, the pharmaceutical composition can contain histidine (e.g. L-histidine) and an excipient such as a sugar (e.g., sucrose or sorbitol). In some embodiments, the concentration of the sugar (e.g., sucrose or sorbitol) is about 10 to about 15 times the concentration of the histidine (e.g., L-histidine). In some embodiments, the concentration of the sugar (e.g., sucrose or sorbitol) is about 13.5 times the concentration of the histidine (e.g., L-histidine).

In some embodiments, the concentration of the sugar (e.g., sucrose or soribitol) is 10 to 15 times the concentration of the histidine (e.g., L-histidine). In some embodiments, the concentration of the sugar (e.g., sucrose or sorbitol) is 13.5 times the concentration of the histidine (e.g., L-histidine).

As provided herein, the pharmaceutical composition can contain a surfactant, for example, a polysorbate. The polysorbate can be, e.g., polysorbate 20 (PS20). In some embodiments, the concentration of the surfactant (e.g., PS20) is about 0.025-0.075% weight by volume (w/v). In some embodiments, the concentration of the surfactant (e.g., PS20) is about 0.035 to about 0.065% w/v. In some embodiments, the concentration of the surfactant (e.g., PS20) is about 0.05% w/v.

In some embodiments, the concentration of the surfactant (e.g., PS20) is 0.025-0.075% weight by volume (w/v). In some embodiments, the concentration of the surfactant (e.g., PS20) is 0.035 to 0.065% w/v. In some embodiments, the concentration of the surfactant (e.g., PS20) is 0.05% w/v.

As provided herein, in some embodiments, the pharmaceutical composition has a pH of about 5 to about 7.5. In some embodiments, the pH of the pharmaceutical composition is about 5.5 to about 7. In some embodiments, the pH of the pharmaceutical composition is about 6.4 to about 7. In some embodiments, the pH of the pharmaceutical composition is about 6.5 to about 7. In some embodiments, the pH of the pharmaceutical composition is about 6.7.

In some embodiments, the pharmaceutical composition has a pH of 5 to 7.5. In some embodiments, the pH of the pharmaceutical composition is 5.5 to 7. In some embodiments, the pH of the pharmaceutical composition is 6.4 to 7. In some embodiments, the pH of the pharmaceutical composition is 6.5 to 7. In some embodiments, the pH of the pharmaceutical composition is 6.7.

As provided herein, the pharmaceutical composition can be a liquid. The pharmaceutical composition (e.g., liquid pharmaceutical composition) can be for parenteral administration, e.g., for intravenous administration.

In one embodiment, the pharmaceutical composition comprises about 5 mg/mL to about 15 mg/mL of CD80 ECD-Fc fusion molecules (e.g., comprising the amino acid sequence of SEQ ID NO:5) in about 15 mM to about 25 mM histidine (e.g., L-histidine), about 225 mM to about 300 mM sucrose or sorbitol, and about 0.025% to about 0.075% PS20. In one embodiment, the pharmaceutical composition has a pH of about 6.4 to about 7 or about 6.5 to about 7, e.g., about 6.7. In one embodiment, the pharmaceutical composition is a liquid.

In one embodiment, the pharmaceutical composition comprises 5 mg/mL to 15 mg/mL of CD80 ECD-Fc fusion molecules (e.g., comprising the amino acid sequence of SEQ ID NO:5) in 15 mM to 25 mM histidine (e.g., L-histidine), 225 mM to 300 mM sucrose or sorbitol, and 0.025% to 0.075% PS20. In one embodiment, the pharmaceutical composition has a pH of 6.4 to 7 or 6.5 to 7, e.g., 6.7. In one embodiment, the pharmaceutical composition is a liquid.

In one embodiment, the pharmaceutical composition comprises about 5 mg/mL to about 15 mg/mL of CD80 ECD-Fc fusion molecules (e.g., comprising the amino acid sequence of SEQ ID NO:5) in about 18 mM to about 22 mM histidine (e.g., L-histidine), about 250 mM to about 290 mM sucrose or sorbitol, and about 0.035% to about 0.065% PS20. In one embodiment, the pharmaceutical composition has a pH of about 6.4 to about 7 or about 6.5 to about 7, e.g., about 6.7. In one embodiment, the pharmaceutical composition is a liquid.

In one embodiment, the pharmaceutical composition comprises 5 mg/mL to 15 mg/mL of CD80 ECD-Fc fusion molecules (e.g., comprising the amino acid sequence of SEQ ID NO:5) in 18 mM to 22 mM histidine (e.g., L-histidine), 250 mM to 290 mM sucrose or sorbitol, and 0.035% to 0.065% PS20. In one embodiment, the pharmaceutical composition has a pH of 6.4 to 7 or 6.5 to 7, e.g., 6.7. In one embodiment, the pharmaceutical composition is a liquid.

In one embodiment, the pharmaceutical composition comprises about 10 mg/mL of CD80 ECD-Fc fusion molecules (e.g., comprising the amino acid sequence of SEQ ID NO:5) in about 20 mM histidine (e.g., L-histidine), about 270 mM sucrose or sorbitol, and about 0.05% PS20. In one embodiment, the pharmaceutical composition has a pH of about 6.7. In one embodiment, the pharmaceutical composition is a liquid.

In one embodiment, the pharmaceutical composition comprises 10 mg/mL of CD80 ECD-Fc fusion molecules (e.g., comprising the amino acid sequence of SEQ ID NO:5) in 20 mM histidine (e.g., L-histidine), 270 mM sucrose or sorbitol, and 0.05% PS20. In one embodiment, the pharmaceutical composition has a pH of 6.7. In one embodiment, the pharmaceutical composition is a liquid.

In some embodiments (including but not limited to any of the above embodiments of pharmaceutical compositions), a pharmaceutical composition comprises CD80 ECD-Fc fusion molecules (e.g., comprising the amino acid sequence of SEQ ID NO:5), wherein the composition comprises no more than 10% of high molecular weight species (HMWS) of the CD80 ECD-Fc fusion molecules and/or no more than 2.5% of low molecular weight species (LMWS) of the CD80 ECD-Fc fusion molecules after 4 weeks at 40° C.

In some embodiments, a pharmaceutical composition comprises CD80 ECD-Fc fusion molecules (e.g., comprising the amino acid sequence of SEQ ID NO:5), wherein the composition comprises about 1% to about 10%, about 1% to about 6%, or about 1% to about 4% HMWS of the CD80 ECD-Fc fusion molecules and/or about 0.5% to about 2.5%, about 0.5% to about 1.6%, or about 0.5% to about 1.5% of LMWS of the CD80 ECD-Fc fusion molecules after 4 weeks at 40° C. In some embodiments, a pharmaceutical composition comprises CD80 ECD-Fc fusion molecules (e.g., comprising the amino acid sequence of SEQ ID NO:5), wherein the composition comprises 1% to 10%, 1% to 6%, or 1% to 4% HMWS of the CD80 ECD-Fc fusion molecules and/or 0.5% to 2.5%, 0.5% to 1.6%, or 0.5% to 1.5% of LMWS of the CD80 ECD-Fc fusion molecules after 4 weeks at 40° C.

In some embodiments, the pharmaceutical composition described above is provided in a syringe or vial. In some embodiments, the syringe or vial comprises about 0.5 to about 5 mls of a pharmaceutical composition provided herein. In some embodiments, the syringe or vial comprises about 1 to about 5 mls of a pharmaceutical composition provided herein.

In some embodiments, the syringe or vial comprises 2 mls of a pharmaceutical composition provided herein Thus, by way of example, a syringe or vial can comprise 20 mg of CD80 ECD-Fc fusion molecules in the 2 ml volume, i.e., about 10 mg/ml of CD80 ECD-Fc fusion molecules. In some embodiments, the syringe or vial comprises 1 ml of a pharmaceutical composition provided herein Thus, by way of example, a syringe or vial can comprise 10 mg of CD80 ECD-Fc fusion molecules in a 1 ml volume, i.e., about 10 mg/ml of CD80 ECD-Fc fusion molecules.

CD80 ECD-Fc Fusion Molecules

Provided herein are pharmaceutical compositions comprising CD80 ECD-Fc fusion molecules. Exemplary CD80 ECD-Fc fusion molecules are provided, for example, in WO 2017/079117, which is herein incorporated by reference in its entirety.

The CD80 ECD can, for example, be a human CD80 ECD. In certain aspects, the human CD80 ECD comprises, consists essentially of, or consists of the amino acid sequence set forth in SEQ ID NO:1.

The Fc domain can be the Fc domain of an IgG. The Fc domain can be the Fc domain of a human immunoglobulin. In certain aspects, the Fc domain is a human IgG Fc domain.

In certain aspects, the Fc domain is a human IgG1 Fc domain. In certain aspects, the human IgG1 Fc domain comprises, consists essentially of, or consists of the amino acid sequence set forth in SEQ ID NO:4.

The CD80 ECD and the Fc domain can be directly linked such that the N-terminal amino acid of the Fc domain follows the C-terminal amino acid of the CD80 ECD. In certain aspects, the CD80 ECD and the Fc domain are translated as a single polypeptide from a coding sequence that encodes both the CD80 ECD and the Fc domain. In certain aspects, the CD80 ECD-Fc fusion molecule comprises a human CD80 ECD and a human IgG1 Fc domain. In certain aspects, the CD80 ECD-Fc fusion molecule comprises, consists essentially of, or consists of the amino acid sequence set forth in SEQ ID NO:5.

CD80 ECD-Fc fusion molecules can, depending on how they are produced, have different levels of particular glycosylation modifications. For example, a CD80 ECD-Fc fusion molecule can be sialylated and can have different amounts of sialic acid (SA) residues.

In certain aspects, a CD80 ECD-Fc fusion molecule (e.g., comprising a human CD80 ECD and a human IgG1 Fc domain, or comprising SEQ ID NO:5) comprises 10 to 60 molecules of SA. In certain aspects, a CD80 ECD-Fc fusion molecule (e.g., comprising a human CD80 ECD and a human IgG1 Fc domain, or comprising SEQ ID NO:5) comprises 15 to 60 molecules of SA. In certain aspects, a CD80 ECD-Fc fusion molecule (e.g., comprising a human CD80 ECD and a human IgG1 Fc domain, or comprising SEQ ID NO:5) comprises 10 to 40 molecules of SA. In certain aspects, a CD80 ECD-Fc fusion molecule (e.g., comprising a human CD80 ECD and a human IgG1 Fc domain, or comprising SEQ ID NO:5) comprises 15 to 30 molecules of SA. In certain aspects, a CD80 ECD-Fc fusion molecule (e.g., comprising a human CD80 ECD and a human IgG1 Fc domain, or comprising SEQ ID NO:5) comprises 15 to 25 molecules of SA. In certain aspects, a CD80 ECD-Fc fusion molecule (e.g., comprising a human CD80 ECD and a human IgG1 Fc domain, or comprising SEQ ID NO:5) comprises 20 to 40 molecules of SA. In certain aspects, a CD80 ECD-Fc fusion molecule (e.g., comprising a human CD80 ECD and a human IgG1 Fc domain, or comprising SEQ ID NO:5) comprises 20 to 30 molecules of SA. In certain aspects, a CD80 ECD-Fc fusion molecule (e.g., comprising a human CD80 ECD and a human IgG1 Fc domain, or comprising SEQ ID NO:5) comprises 30 to 40 molecules of SA. In certain aspects, a CD80 ECD-Fc fusion molecule (e.g., comprising a human CD80 ECD and a human IgG1 Fc domain, or comprising SEQ ID NO:5) comprises 10, 15, 20, 25, 30, 35, or 40 molecules of SA. In certain aspects, a CD80 ECD-Fc fusion molecule (e.g., comprising a human CD80 ECD and a human IgG1 Fc domain, or comprising SEQ ID NO:5) comprises at least 15 molecules of SA. In certain aspects, a CD80 ECD-Fc fusion molecule (e.g., comprising a human CD80 ECD and a human IgG1 Fc domain, or comprising SEQ ID NO:5) comprises at least 20 molecules of SA. In certain aspects, a CD80 ECD-Fc fusion molecule (e.g., comprising a human CD80 ECD and a human IgG1 Fc domain, or comprising SEQ ID NO:5) comprises at least 25 molecules of SA. In certain aspects, a CD80 ECD-Fc fusion molecule (e.g., comprising a human CD80 ECD and a human IgG1 Fc domain, or comprising SEQ ID NO:5) comprises at least 30 molecules of SA. In certain aspects, a CD80 ECD-Fc fusion molecule (e.g., comprising a human CD80 ECD and a human IgG1 Fc domain, or comprising SEQ ID NO:5) comprises at least 35 molecules of SA. In certain aspects, a CD80 ECD-Fc fusion molecule (e.g., comprising a human CD80 ECD and a human IgG1 Fc domain, or comprising SEQ ID NO:5) comprises at least 40 molecules of SA.

Therapeutic Uses and Methods

In one aspect, provided herein are methods for treating a solid tumor in a subject (e.g., a human subject), comprising administering to a subject in need thereof a pharmaceutical composition provided herein comprising CD80 ECD-Fc fusion molecules.

In a certain embodiment, provided herein are pharmaceutical compositions for treating a solid tumor selected from the group consisting of: a colorectal cancer, breast cancer, gastric cancer, non-small cell lung cancer, small cell lung cancer, melanoma, squamous cell carcinoma of the head and neck, ovarian cancer, pancreatic cancer, renal cell carcinoma, hepatocellular carcinoma, bladder cancer, or endometrial cancer. In certain embodiments, the solid tumor is a renal cell carcinoma. In certain embodiments, the solid tumor is a melanoma.

The solid tumor can be, for example, an advanced solid tumor. In certain instances, the solid tumor is not a primary central nervous system tumor.

The patient to be treated according to the methods provided herein may have received prior therapy with at least one PD-1/PD-L1 antagonist selected from a PD-1 antagonist and a PD-L1 antagonist. The PD-1/PD-L1 antagonist can be, for example, nivolumab, pembrolizumab, atezolizumab, durvalumab, or avelumab. The PD-1/PD-L1 antagonist may have been administered in an advanced or metastatic setting. In other instances, the patient to be treated according to the methods provided herein has not received prior therapy with a PD-1/PD-L1 antagonist.

The patient to be treated according to the methods provided herein may have received prior therapy with an anti-angiogenic agent. The anti-angiogenic agent can be, for example, sunitinib, sorafenib, pazopanib, axitinib, tivozanib, ramucirumab, or bevacizumab. The anti-angiogenic agent may have been administered in an advanced or metastatic setting.

The patient to be treated according to the methods provided herein, for example a patient with a melanoma, may have a BRAF mutation. The patient may have received prior therapy with a BRAF inhibitor. The BRAF inhibitor can be, for example, vemurafenib and dabrafenib. The BRAF inhibitor may have been administered in an advanced or metastatic setting.

The tumor to be treated according to the methods provided herein can be recurrent or progressive after a therapy selected from surgery, chemotherapy, radiation therapy, and a combination thereof.

The tumor to be treated according to the methods provided herein can be resistant or non-responsive to a PD-1/PD-L1 antagonist, such as nivolumab, pembrolizumab, atezolizumab, durvalumab, or avelumab. The tumor to be treated according to the methods provided herein can be resistant or non-responsive to an anti-angiogenic agent, such as sunitinib, sorafenib, pazopanib, axitinib, tivozanib, ramucirumab, or bevacizumab. The tumor to be treated according to the methods provided herein can be resistant or non-responsive to a BRAF inhibitor, such as vemurafenib or dabrafenib.

The tumor to be treated according to the methods provided herein can be refractory to a PD-1/PD-L1 antagonist, such as nivolumab, pembrolizumab, atezolizumab, durvalumab, or avelumab. The tumor to be treated according to the methods provided herein can be refractory to an anti-angiogenic agent, such as sunitinib, sorafenib, pazopanib, axitinib, tivozanib, ramucirumab, or bevacizumab. The tumor to be treated according to the methods provided herein can be refractory to a BRAF inhibitor, such as vemurafenib or dabrafenib.

The tumor to be treated according to the methods provided herein can be recurrent after treatment with a PD-1/PD-L1 antagonist, such as nivolumab, pembrolizumab, atezolizumab, durvalumab, or avelumab. The tumor to be treated according to the methods provided herein can be recurrent after treatment with an anti-angiogenic agent, such as sunitinib, sorafenib, pazopanib, axitinib, tivozanib, ramucirumab, or bevacizumab. The tumor to be treated according to the methods provided herein can be recurrent after treatment with a BRAF inhibitor, such as vemurafenib or dabrafenib.

The pharmaceutical compositions described herein can be delivered to a patient by an intravenous route. Usually, the patient is a human but non-human mammals including transgenic mammals can also be treated.

EXAMPLES

The examples in this Section (i.e., Section 6) are offered by way of illustration, and not by way of limitation.

Example 1: Methods Used in the Formulation Studies

I. General Formulation Procedure

A human CD80 ECD-human IgG1 Fc fusion protein comprising the amino acid sequence of SEQ ID NO:5 (referred to hereinafter as "hCD80-Fc") was expressed in and purified from a CHO cell line. Samples of the hCD80-Fc were prepared in various formulations by dialysis of the polysorbate free drug substance using 20 kD molecular weight cut off (MWCO) dialysis membrane. After dialysis, concentration of hCD80-Fc was measured by UV spectroscopy using extinction coefficient of $1.35$ $cm^{-1}[g/L]^{-1}$. The protein concentrations of the buffer exchanged samples were adjusted to desired values with dialysis buffer and 10% Polysorbate 20 (PS20) stock solution was spiked into each formulation for a final concentration of 0.05% (w/v) PS20. Formulations were sterile filtered using 0.22 μm filter units and filled into appropriate container/closure systems in a laminar flow hood. Samples were placed at various storage conditions per study design and were pulled at pre-determined time points for stability analysis using various methods.

II. Analytical Methods

Visual inspection: Visual assessment was made against both black and white backgrounds under fluorescence lighting. Samples were examined for color, clarity and presence of visible particles.

Protein Concentration: Protein concentration was determined by UV absorbance at 280 nm using theoretical absorption coefficients of $1.35$ $cm^{-1}[g/L]^{-1}$. Samples were diluted to within the linear range of absorbance with Dulbecco's Phosphate Buffer Saline (DPBS) and measured against DPBS as blank. Absorbance was measured using Agilent Cary 8454 UV-Vis Spectrophotometer (Agilent Technologies, CA).

pH: Buffer pH was determined using a calibrated Beckman Coulter pHi560 meter (Beckman Coulter, Inc., CA).

Osmolality: Buffer osmolality was measured by vapor pressure using a Wescor VAPRO system (Wescor, Inc., UT).

Differential Scanning calorimetry (DSC) Analysis: DSC measurements were performed on a MicroCal VP-Capillary DSC platform (GE Healthcare, UK). The protein samples were diluted in respective formulation buffers to a concentration of 1 mg/mL. Matched formulation buffer was used as a reference. The samples were scanned from 15° C. to 110° C. at a rate of 1° C./min. Data were first normalized for protein concentration, then baseline corrected, and buffer subtracted using Origin 7.0 software (OriginLab, MA). Melting transitions were analyzed with cursor-initiated DSC peak fit function using non-two-state unfolding model within the origin software.

Unfolding Temperature (Tm) by UNit system: The unfolding temperature (Tm) of a protein provides a measurement of the physical stability of the molecule. Unfolding temperature is defined as the temperature at which equal amount of native and denatured protein exists in equilibrium. UNit system by Unchained Labs (Pleasanton, CA) uses intrinsic fluorescent spectroscopic changes to determine the temperature at which the heat induced unfolding of a protein occurs. Samples at 1 mg/mL were scanned from 20° C. to 90° C. at a rate of 1° C./min. Tm were determined using UNcle software from Unchained Labs.

Imaged Capillary Isoelectric Focusing (iCIEF): The charge variants were analyzed by Imaged capillary isoelectric focusing (iCIEF) on Protein Simple iCE3 instrument with 720 NV auto-sampler (ProteinSimple, San Jose, CA). Data were analyzed using iCIEF CFR software and relative amount of main, acidic and basic peaks was determined by integrating the area of the peaks observed in the profile.

Size-Exclusion High Performance Liquid Chromatography (SE-HPLC): Samples were analyzed on Agilent 1100 Series HPLC equipped with a diode array detector and absorbance was monitored at 280 nm. Samples were diluted to 1 mg/ml in mobile phase (100 mM sodium phosphate, 400 mM sodium chloride pH 6.8), and 50 μL was injected onto a pre-equilibrated Sepax Zenix SEC-300 7.8×200 mm column (Sepax Technologies, Inc., Delaware). The SEC separation and guard columns were used at 25° C. A flow rate of 1.0 mL/min was used with a 12-min run time. Aggregate, monomer, and fragment peaks were quantified using instrument software for data analysis.

Capillary Electrophoresis with Sodium Dodecyl Sulfate Gel (CE-SDS): CE-SDS method was used to determine the purity under reduced and non-reduced conditions. Samples were analyzed on Beckman Coulter PA800 plus system (Beckman Coulter, CA) using uncoated 50 μM I.D. capillary. Absorbance was monitored at 220 nm. Purity of hCD80-Fc under reduced condition was determined by measuring the peak area of the single-chain monomer peak and comparing with the total area of all detected peaks. Purity of hCD80-Fc under non-reduced condition was determined by measuring the peak area of the main intact protein peak and comparing it with the total area of all detected peaks.

Subvisible Particulate Matters by HIAC: An HIAC 9703+ particle counter (Hach, Loveland, Colorado), equipped with an HRDL-150 detector and 1 mL syringe was used. Before use, the system was flushed with particle free Milli-Q water (Millipore, MA) to generate a clean base line. Four consecutive 0.4 mL aliquots were taken from samples, and particle counts from last three aliquots were averaged and reported.

CTLA4 Binding ELISA: An ELISA method was used to determine the relative potency of hCD80-Fc on the basis of the specific and quantitative binding of hCD80-Fc to recombinant human Cytotoxic T-Lymphocyte Antigen 4 (CTLA-4) protein against a Reference Material (RM). In this assay, the 96-well microplate was coated with a recombinant form of human CTLA-4 protein. After blocking with 1% BSA buffer, the hCD80-Fc RM, Control Sample, and test samples at serial dilutions are added to the plate and incubated with the coating ligand. With washes, a horseradish peroxidase (HRP) conjugated mouse anti-human Fc secondary antibody, a secondary antibody-HRP, and TMB substrate was added to the plate sequentially. The ELISA plate was read to measure the absorbance signal at 450 nm using a plate reader. Relative Potency (RP) is calculated based on the $EC_{50}$ values of the RM and test samples and reported accordingly.

CD28 Cell-based Bioassay: Method QM5963 is based on Promega's T-cell activation assay (IL-2) (Madison, WI), which utilizes Jurkat T-cells stably transfected with a Luciferase reporter driven by an IL-2 promoter. Activator cells (HEK293-OKT3-CD64) and effector cells (provided by Promega's kit) are thawed and re-suspended in IL-2 Luciferase Reporter Assay Buffer, plated and incubated with hCD80-Fc Reference Material (RM), Test Sample (TS) and Assay Control Standard (ACS) dilutions overnight (18-22 hours). During incubation, hCD80-Fc binds to surface localized CD64 (activator cells) and CD28 (effector cells), which in tandem with OKT3/CD3 engagement, triggers activation of the IL-2 Luc pathway driving an increase in Luciferase expression. The extent of the signaling response is proportional to the amount of hCD80-Fc present at each dilution hCD80-Fc is a Fc fusion protein comprising the amino acid sequence of SEQ ID NO:5. A knowledge-based formulation development approach was used to identify the appropriate compositions that provide maximal stability for the protein. To do this, both intrinsic properties of the molecule and extrinsic formulation components that could affect the stability of the protein were considered.

Figure 5A:
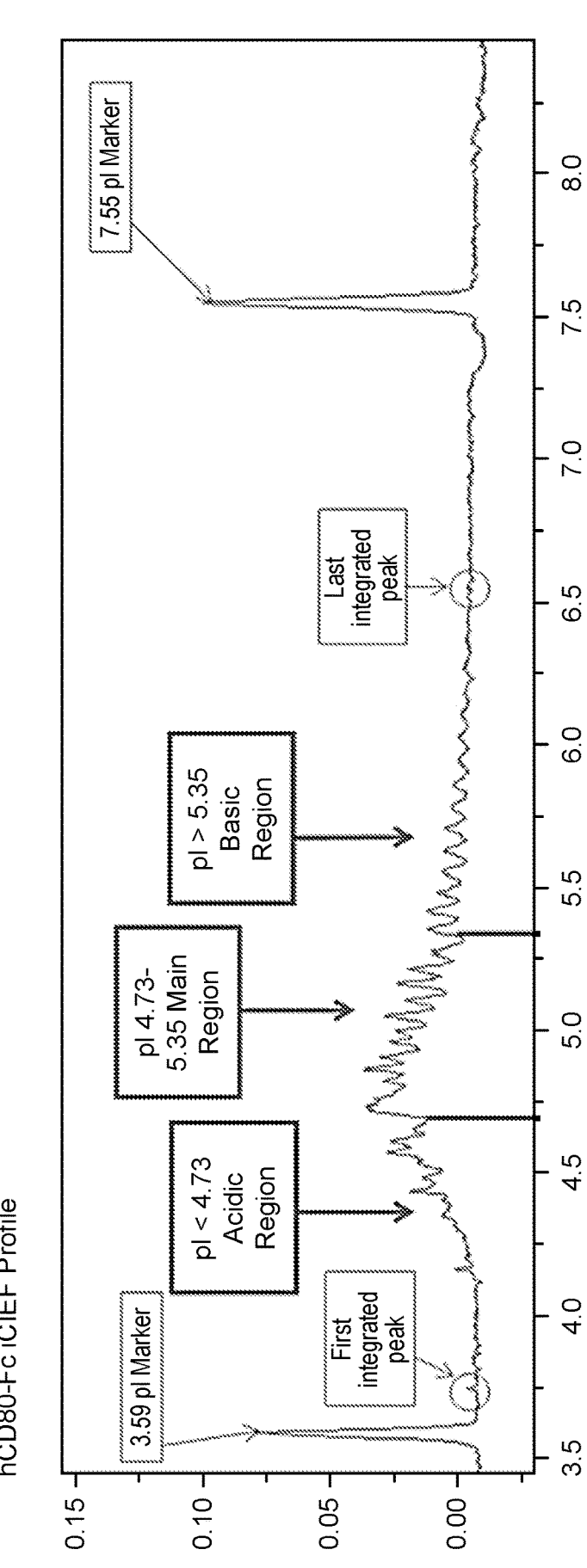
FIG. 5A shows the charge profile of hCD80-Fc as determined by imaged Capillary Isoelectric Focusing (iCIEF).
Figure 5B:
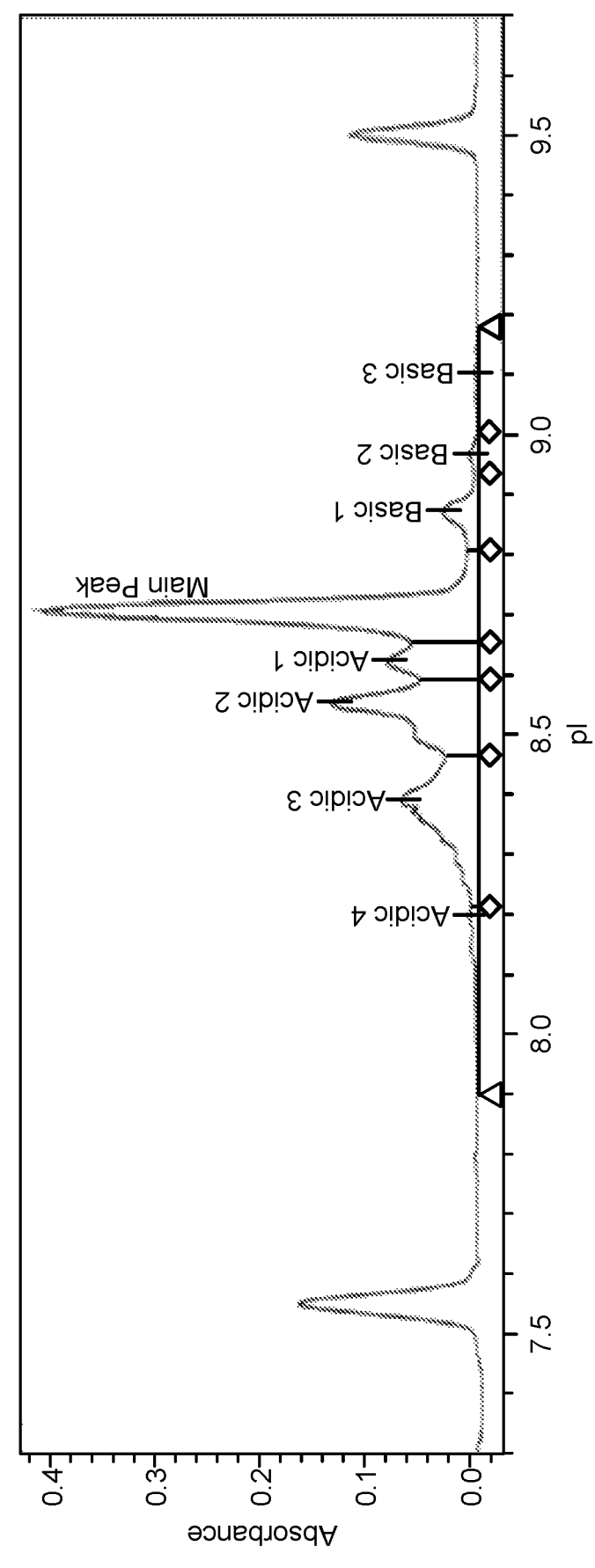
FIG. 5B shows the charge profile of a typical therapeutic antibody as determined by iCIEF. (See Example 4.)

The primary amino acid sequence of hCD80-Fc is shown in Table 1. The theoretical pI of hCD80-Fc protein is 6.0. However, the presence of sialic acid on this highly glycosylated protein could reduce the actual pI. Indeed, the iCIEF analysis of hCD80-Fc generated complex results due to the presence of sialic acid on the protein. As shown in FIG. 5A, the iCIEF generated a range of peaks, representing a pI broadly ranging from about 4.0-6.5, with an acidic region (pI<4.73), a main region (pI 4.73-5.35), and a basic region (pI>5.35). (Note the two pI markers at 3.59 and 7.55.) As a comparison, FIG. 5B shows the iCIEF profile of a typical therapeutic monoclonal antibody, which shows a strong main peak and several distinct charge variant peaks. Changes in the charge profile of hCD80-Fc were therefore not reasonably identifiable using iCIEF, and that method could not be used for further formulation selection. Without iCIEF as a tool to determine charge variants, it is more challenging to develop a suitable formulation with long term stability.

Given these results, an initial screen of formulations ranging between pH 4-7.5 was planned using methodology other than iCIEF.

TABLE 1

| Primary Amino Acid Sequence of hCD80-Fc |
| --- |

| Sequence Designation | Sequence (SEQ ID NO) |
| --- | --- |
| hCD80-Fc | VIHVTKEVKEVATLSCGHNVSVEELAQTRIYWQKEKKMVLTMMSG<br>DMNIWPEYKNRTIFDITNNLSIVILALRPSDEGTYECVVLKYEKDAFK<br>REHLAEVTLSVKADFPTPSISDFEIPTSNIRRIICSTSGGFPEPHLSWLE<br>NGEELNAINTTVSQDPETELYAVSSKLDFNMTTNHSFMCLIKYGHLR<br>VNQTFNWNTTKQEHFPDNEPKSSDKTHTCPPCPAPELLGGPSVFLFP<br>PKPKDTLMISRTPEVTCVVVDVSHEDPEVKFNWYVDGVEVHNAKT<br>KPREEQYNSTYRVVSVLTVLHQDWLNGKEYKCKVSNKALPAPIEKT<br>ISKAKGQPREPQVYTLPPSRDELTKNQVSLTCLVKGFYPSDIAVEWE<br>SNGQPENNYKTTPPVLDSDGSFFLYSKLTVDKSRWQQGNVFSCSVM<br>HEALHNHYTQKSLSLSPGK (SEQ ID NO: 5) | level, which is quantified by addition of Bio-Glo™ Luciferase Assay reagents and enumeration by a plate reader with glow-type luminescence reading.

Example 2: Biochemical Analysis of Amino Acid Residues of hCD80-Fc

Among protein therapeutics, Fc fusion proteins are generally more challenging to formulate than antibodies (e.g., monoclonal antibodies), because the latter has a Fab portion that is relatively stable, whereas Fc fusion proteins contain protein structure outside of the Fc that could potentially confer more complexity and decreased stability. Compared with monoclonal antibodies, a relatively small number of Fc fusion proteins have received FDA approval. Specifically, a total of eleven Fc fusion proteins were approved by late 2017, compared with a total of about 73 monoclonal antibodies by that time. (See, e.g., Jafari et al (2017) Curr. Med. Chem. 24, 1228-1237; and https://www.creative-biolabs.com/blog/index.php/new-monoclonal-antibody-drug-approvals-in-2017/, posted Feb. 8, 2018.)

Analysis of the primary sequence of hCD80-Fc revealed that some amino acid residues could potentially undergo biochemical modifications. These include deamidation in asparagine, isomerization in aspartic acid, and oxidation in methionine, cysteine, histidine, tryptophan, phenylalanine, and tyrosine. The potential biochemical degradation spots in hCD80-Fc are indicated in bold in the sequence of Table 1. The underlined amino acid sequence in Table 1 indicates the Fc (IgG1) region. The potential biochemical degradation spots are noted in Table 2.

TABLE 2

| Potential Amino Acid Residues in hCD80-Fc for Chemical Degradation Pathways. | | |
| --- | --- | --- |
| Degradation Pathways | Sites | Number of sites |
| Deamidation | Asparagine-Glycine | 3 |
| | Asparagine-Serine | 1 |
| | Asparagine-Asparagine | 2 |

TABLE 2-continued

Potential Amino Acid Residues in hCD80-Fc
for Chemical Degradation Pathways.

| Degradation Pathways | Sites | Number of sites |
|---|---|---|
| Isomerization | Aspartic acid-Glycine | 2 |
| | Aspartic acid-Serine | 0 |
| Oxidation | Methionine | 8 |
| | Histidine | 14 |
| | Tryptophan | 8 |
| | Cysteine | 10 (even number) |
| | Tyrosine | 15 |
| | Phenylalanine | 16 |

To develop a liquid formulation that could provide good stability for hCD80-Fc, different conditions such as pH, buffer types, and excipients were evaluated. The stability of the protein was monitored based on the biophysical and biochemical properties of hCD80-Fc in each study. The details of the studies and their results are described here.

Example 3: Initial pH Screening Study

Formulation pH plays a significant role in protein stability, influencing biochemical degradation pathways such as deamidation, isomerization and oxidation, as well as biophysical degradations such as aggregation and fragmentation due to interactions between proteins and with their environment. A pH screen study was conducted to determine a pH range that provides stability for hCD80-Fc and to understand the degradation mechanisms of the protein under these conditions. The details of the formulation compositions evaluated in the study are listed in Table 3. The material used in this study was provided after Protein A purification.

TABLE 3

Formulations Evaluated for pH Effect on Protein Stability

| # | hCD80-Fc (mg/mL) | Formulation | % PS20 (w/v) | pH |
|---|---|---|---|---|
| 1 | 1.0 | 20 mM Citrate, 142 mM Arginine | 0.05 | 4.0 |
| 2 | 1.0 | 20 mM Citrate, 142 mM Arginine | 0.05 | 5.0 |
| 3 | 1.0 | 20 mM Histidine, 142 mM Arginine | 0.05 | 6.7 |
| 4 | 1.0 | 20 mM Phosphate, 142 mM Arginine | 0.05 | 7.5 |

The stability of hCD80-Fc at different pH was evaluated under temperature conditions of 5° C., 25° C., and 40° C. for up to 11 days. All samples remained clear and colorless with no particles observed for the duration of the study. Changes in aggregates and fragments were determined by size exclusion high-performance liquid chromatography (SE-HPLC). SE-HPLC assay separates protein molecules by size. The monomer peak is identified as the protein with the expected size at its retention time. Aggregates or HMW peak(s) come before than the monomer peak. Fragments or LMW peaks come after the monomer peak.

Figure 2:
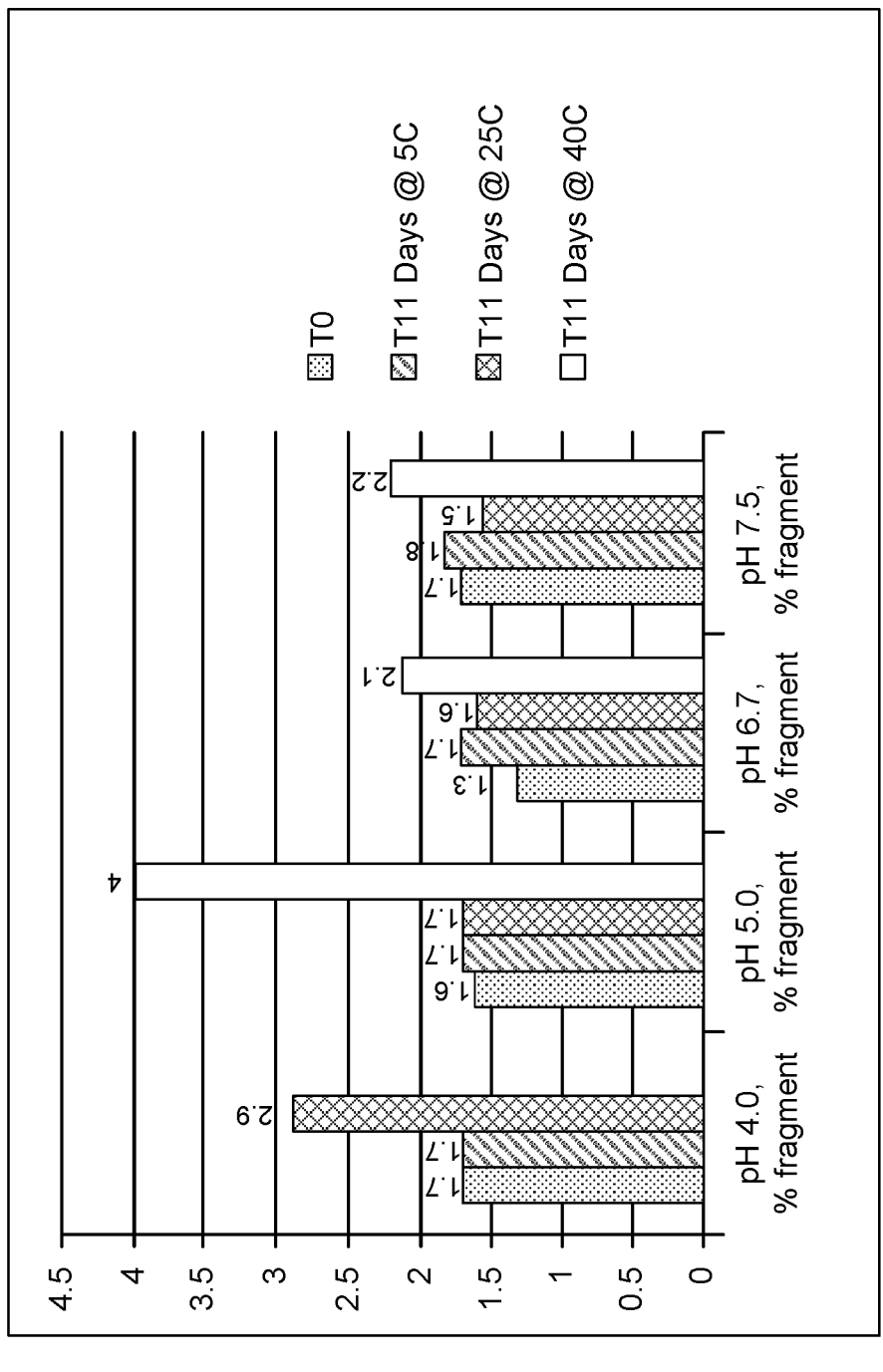
FIG. 2 shows the impact of buffer pH on fragment formation as determined by SE-HPLC. (See Example 3.)

At T0, about 8-9% aggregates were observed for hCD80-Fc at 1 mg/ml concentration in the formulations studied. After 11 days at 40° C. the soluble aggregates increased noticeably in the pH 4, 5, and 7.5 formulations, but only a small increase of aggregates was observed in the pH 6.7 formulation (FIG. 1). Slightly more fragments were observed in formulations of pH 4 or 5 compared with those of pH 6.7 or 7.5 (FIG. 2). The results from this study showed that hCD80-Fc is most stable around pH 5-7.5 as indicated by SE-HPLC.

Example 4: Detailed pH Screening Study

The results of the preliminary pH screening study showed that hCD8O-Fc was more stable around pH 5-7.5. An additional pH study was carried out to identify the pH that provides maximum stability in the range of pH 5.5 to 7.0. The formulations of the compositions that were tested are listed in Table 4. All formulations contained 270 mM sucrose and 0.05% polysorbate 20. The stability of hCD80-Fc at 1 mg/mL was examined based on visual appearance, aggregation and fragmentation (by SE-HPLC), and charge variants (iCIEF) under stressed (40° C.) conditions for up to four weeks.

TABLE 4

Formulations Evaluated for Detailed pH Effect on Protein Stability

| # | Formulations | % PS20 (w/v) | pH | Concentration (mg/mL) |
|---|---|---|---|---|
| 1 | 20 mM Citrate, 270 mM Sucrose | 0.05 | 5.5 | 1 |
| 2 | 20 mM L-Histidine, 270 mM Sucrose | 0.05 | 6.0 | 1 |
| 3 | 20 mM L-Histidine, 270 mM Sucrose | 0.05 | 6.5 | 1 |
| 4 | 20 mM Phosphate, 270 mM Sucrose | 0.05 | 7.0 | 1 |

To determine the thermal stability of hCD80-Fc under different pH conditions, the unfolding temperature was measured by intrinsic fluorescent change using a UNit instrument in a separate study. The shift in tryptophan fluorescence emission wavelength indicates that an unfolding event occurs when samples are heated. Table 5 shows the measured unfolding temperature (Tm1) of hCD80-Fc under different pH conditions. Since this study focused on overall stability of hCD80-Fc and not on domain-dependent unfolding, only the lowest Tm (Tm1) by UNit system was reported. The results indicate that Tm1 is hardly pH dependent, so that formulation compositions at pH 5.5-7.0 will provide similar thermal stability. The effect of formulation compositions at pH 5.5-7.0 on colloidal stability remains to be determined.

TABLE 5 hCD80-Fc unfolding temperature (Tm1)
at different pH as measured by UNit

| # | Formulation | pH | % PS20 | Tm1 (° C.) |
|---|---|---|---|---|
| 1 | 20 mM Sodium Citrate, 270 mM Sucrose | 5.5 | 0.05 | 61.6 |
| 2 | 20 mM Histidine, 270 mM Sucrose | 6.0 | 0.05 | 60.8 |
| 3 | 20 mM Histidine, 270 mM Sucrose | 6.5 | 0.05 | 60.6 |
| 4 | 20 mM Histidine, 270 mM Sucrose | 7.0 | 0.05 | 60.7 |

Figure 3:
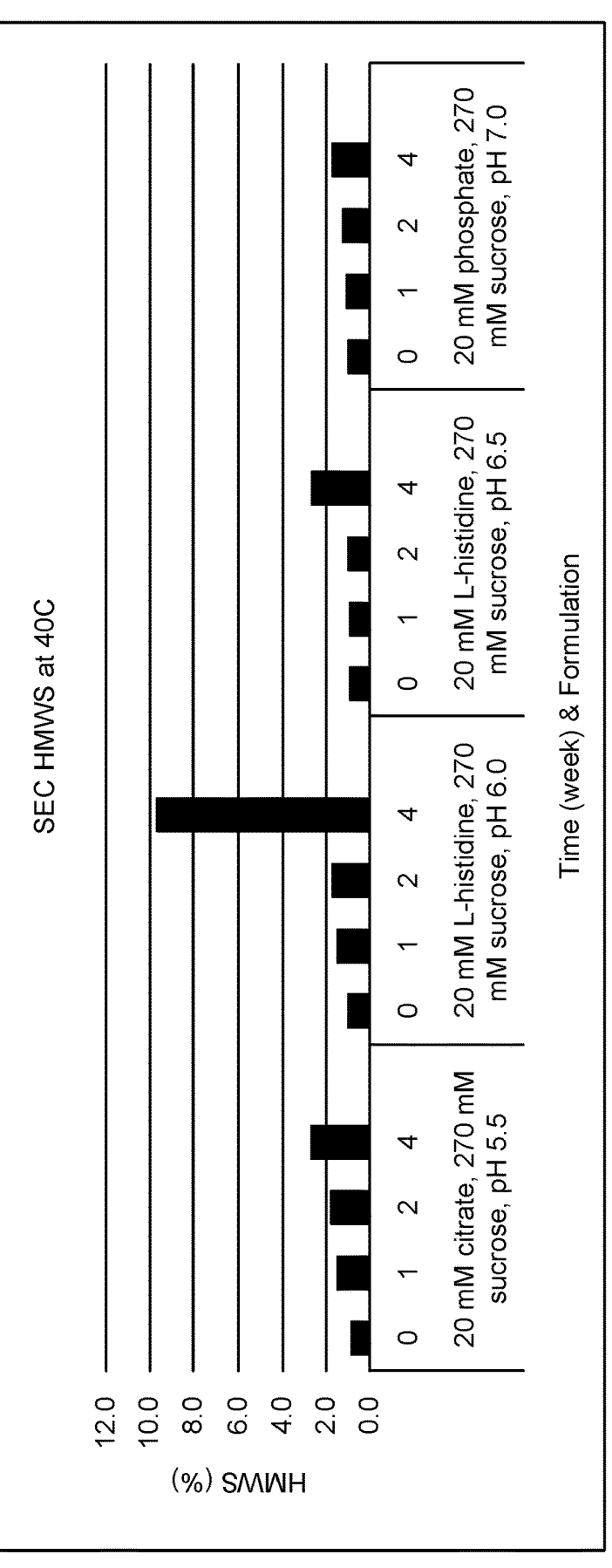
FIG. 3 shows the impact of buffer pH on aggregate formation at 40° C. as determined by SE-HPLC. (See Example 4.)
Figure 4:
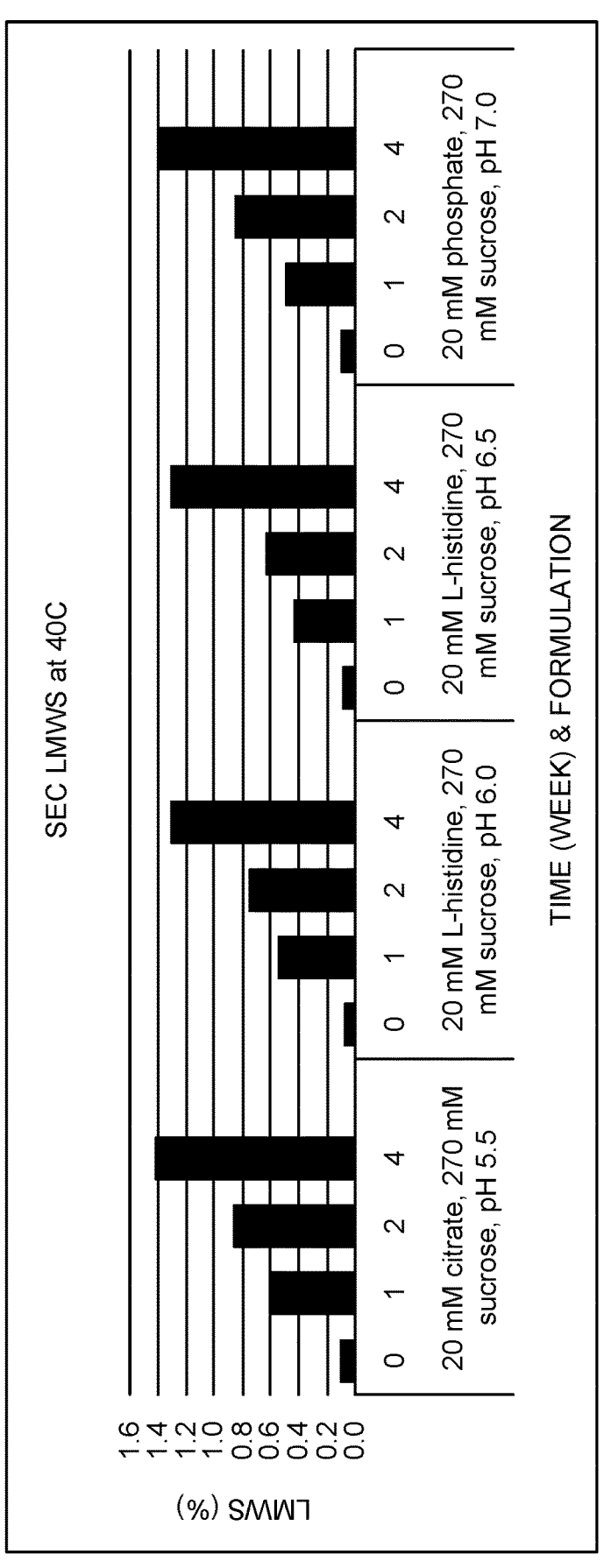
FIG. 4 shows the impact of buffer pH on fragment formation at 40° C. as determined by SE-HPLC. (See Example 4.)

All samples remained clear and colorless with no particles observed for the duration of the study. SE-HPLC results showed that low levels of aggregates were observed for hCD80-Fc at 1 mg/ml concentration at T0. Thermal stress of four weeks at 40° C. resulted in a pH-dependent increase in aggregation in the order of pH 7.0<6.5=5.5<6.0 (FIG. 3). The cause of higher amount of aggregates observed at pH 6.0 remains to be determined. No significant differences in the fragmentation were observed in different pH conditions (FIG. 4).

Collectively, the study results indicate that formulations at pH 6.0-7.0 will likely provide the best control of aggregate and fragment formation for hCD80-Fc Example 5: Buffer Species Screening Study Like pH, buffer types influence protein stability to various extents. Citrate and histidine are two frequently used buffer species whose effective pH range is between 5.5 and 7.0 based on their pKa. The accelerated stability of hCD80-Fc at 10 mg/mL was evaluated in citrate and histidine buffers from pH 5.5 to pH 7.0 in 0.5-unit increments, with the aim of determining a buffer that will provide maximal stability at pH 5.5-7.0. A protein concentration of 10 mg/mL was used in this study to confirm the pH effect observed at the 1 mg/mL protein concentration. The formulation compositions are provided in Table 6. These buffers were examined for their effect on protein stability at 25° C. for up to 3 months and 40° C. for up to 2 months based on appearance, aggregation, and fragmentation.

TABLE 6

Formulation Buffer Species Evaluated for Protein Stability

| # | Formulations | % PS20 | pH | Concentration (mg/mL) |
|---|---|---|---|---|
| F1 | 20 mM Citrate, 270 mM Sucrose | 0.05 | 5.5 | 10 |
| F2 | 20 mM Citrate, 270 mM Sucrose | 0.05 | 6.0 | 10 |
| F3 | 20 mM Citrate, 270 mM Sucrose | 0.05 | 6.5 | 10 |
| F4 | 20 mM Histidine, 270 mM Sucrose | 0.05 | 6.0 | 10 |
| F5 | 20 mM Histidine, 270 mM Sucrose | 0.05 | 6.5 | 10 |
| F6 | 20 mM Histidine, 270 mM Sucrose | 0.05 | 7.0 | 10 |

Figure 6:
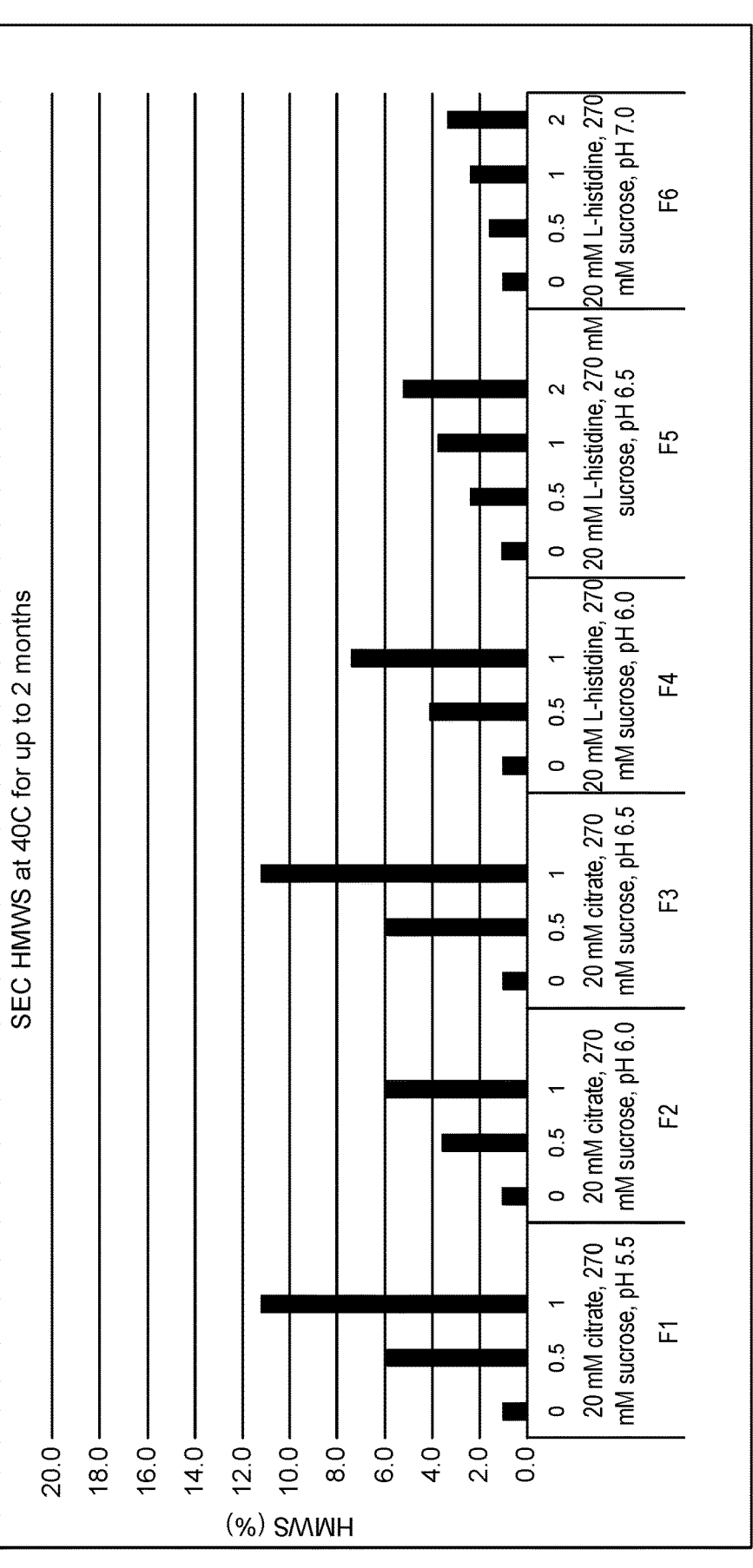
FIG. 6 shows the effect of citrate and histidine buffers on aggregate formation at 40° C. as determined by SE-HPLC. (See Example 5.)
Figure 7:
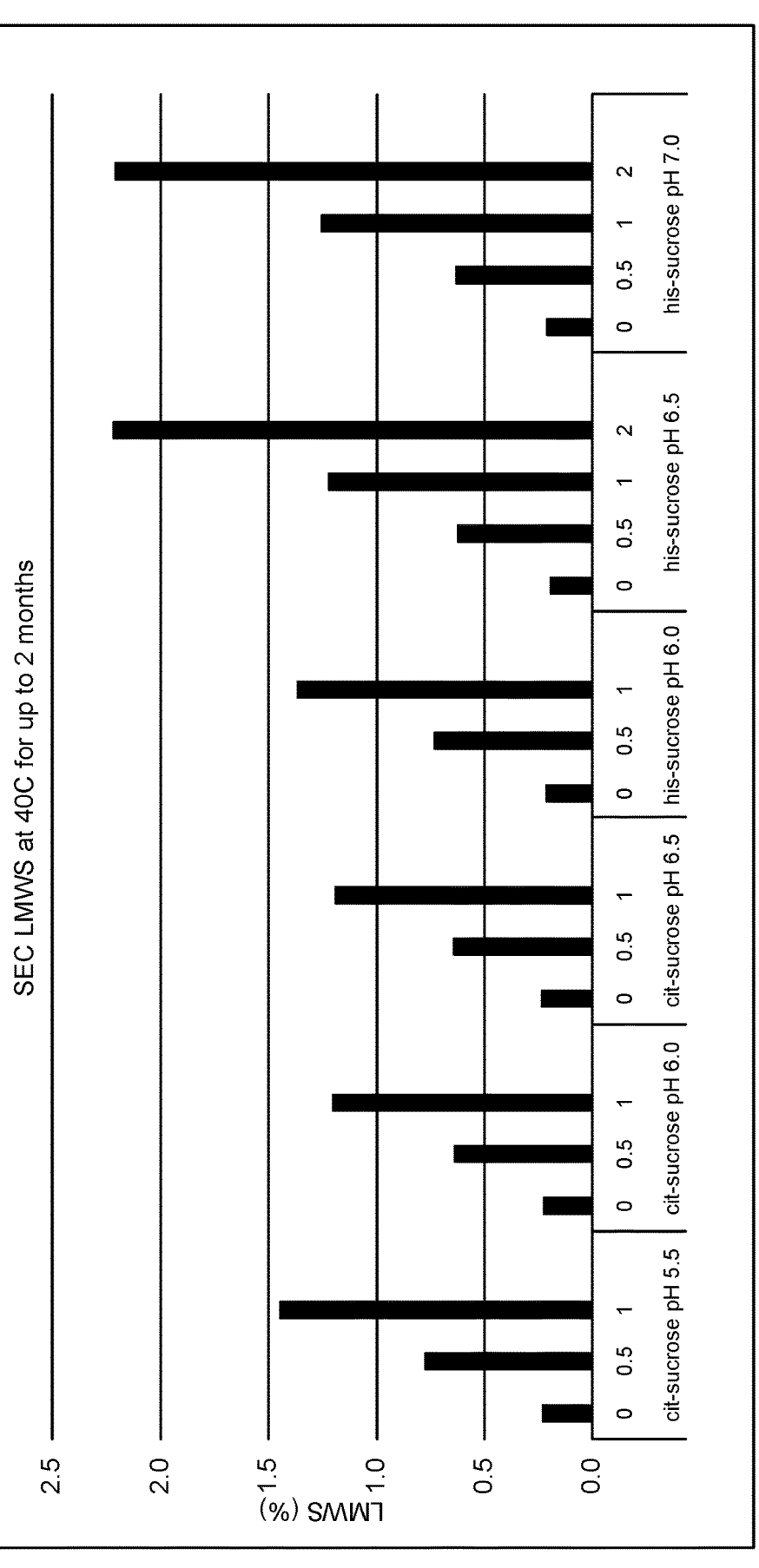
FIG. 7 shows the effect of citrate and histidine buffers on fragment formation at 40° C. as determined by SE-HPLC. (See Example 5.)

All samples remained clear and colorless with no particles observed for the duration of the study. Among citrate and histidine-based formulations within pH 5.5-7.0, less aggregates were observed in histidine formulations compared with citrate formulations. In particular, histidine-based formulations at pH 6.5 and 7.0 are more desirable compared with other formulations based on SE-HPLC results shown in FIG. 6. Similar levels of fragments were observed in all formulations evaluated (FIG. 7).

Based on these results, it is concluded that hCD80-Fc is more stable in histidine buffer at pH 6.5-7.0 than other formulations tested.

Example 6: Excipients Selection Study

Formulation excipients such as bulking agents can affect product stability. To assess the effect of excipients on hCD80-Fc stability, 1 mg/mL of hCD80-Fc was formulated into citrate, histidine, and phosphate formulations containing arginine, sucrose, or NaCl at isotonic concentrations. Citrate formulations were formulated at pH 5.5; histidine formulations were formulated at pH 6.0 or 6.5; phosphate formulations were formulated at pH 7.0. The detailed formulation compositions are provided in Table 7. The excipients were examined for their effect on protein stability based on visual appearance, aggregation, and fragmentation under the storage conditions of 5° C. and 25° C. for 3 months and 40° C. for up to 2 months.

TABLE 7

Formulation Excipients Evaluated For
Protein Stability in Various Buffers

| ID | Buffer | Excipients | pH | Polysorbate 20 | Concentration (mg/mL) |
|---|---|---|---|---|---|
| 1 | 20 mM Citrate | 142 mM Arginine | 5.5 | 0.05% | 1 |
| 2 | | 270 mM Sucrose | | 0.05% | 1 |
| 3 | 20 mM | 142 mM Arginine | 6.0 | 0.05% | 1 |

TABLE 7-continued

Formulation Excipients Evaluated For
Protein Stability in Various Buffers

| ID | Buffer | Excipients | pH | Polysorbate 20 | Concentration (mg/mL) |
|---|---|---|---|---|---|
| 4 | Histidine | 270 mM Sucrose | | 0.05% | 1 |
| 5 | | 140 mM NaCl | | 0.05% | 1 |
| 6 | 20 mM | 142 mM Arginine | 6.5 | 0.05% | 1 |
| 7 | Histidine | 270 mM Sucrose | | 0.05% | 1 |
| 8 | | 140 mM NaCl | | 0.05% | 1 |
| 9 | 20 mM | 142 mM Arginine | 7.0 | 0.05% | 1 |
| 10 | Phosphate | 270 mM Sucrose | | 0.05% | 1 |

Another study was performed to compare the sucrose and sorbitol on hCD80-Fc stability using histidine-based formulations at pH 6.0, 6.5, and 7.0. The formulation compositions are provided in Table 8. The excipients were examined for their effect on protein stability based on visual appearance, aggregation, and fragmentation under the storage conditions of 5° C. and 25° C. for 3 months and 40° C. for up to 2 months.

TABLE 8

Formulation Excipients Evaluated for
Protein Stability in Histidine Buffers

| ID | Buffer | Excipients | pH | Polysorbate 20 | Concentration (mg/mL) |
|---|---|---|---|---|---|
| 11 | 20 mM | 270 mM Sucrose | 6.0 | 0.05% | 10 |
| 12 | Histidine | 4.7% Sorbitol | | 0.05% | 10 |
| 13 | 20 mM | 270 mM Sucrose | 6.5 | 0.05% | 10 |
| 14 | Histidine | 4.7% Sorbitol | | 0.05% | 10 |
| 15 | 20 mM | 270 mM Sucrose | 7.0 | 0.05% | 10 |
| 16 | Histidine | 4.7% Sorbitol | | 0.05% | 10 |

Figure 8:
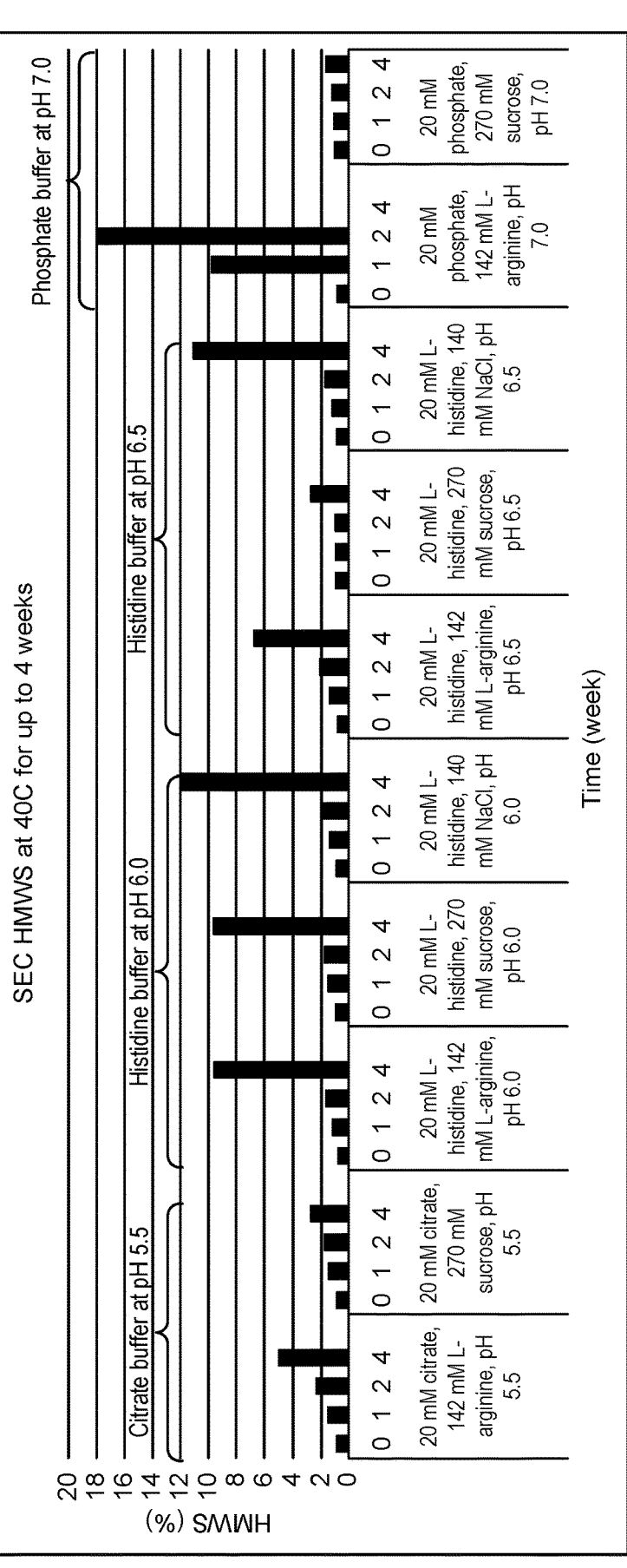
FIG. 8 shows the effect of arginine, sucrose, and NaCl on aggregate formation in 1 mg/ml hCD80-Fc at 40° C. as determined by SE-HPLC. (See Example 6.)
Figure 9:
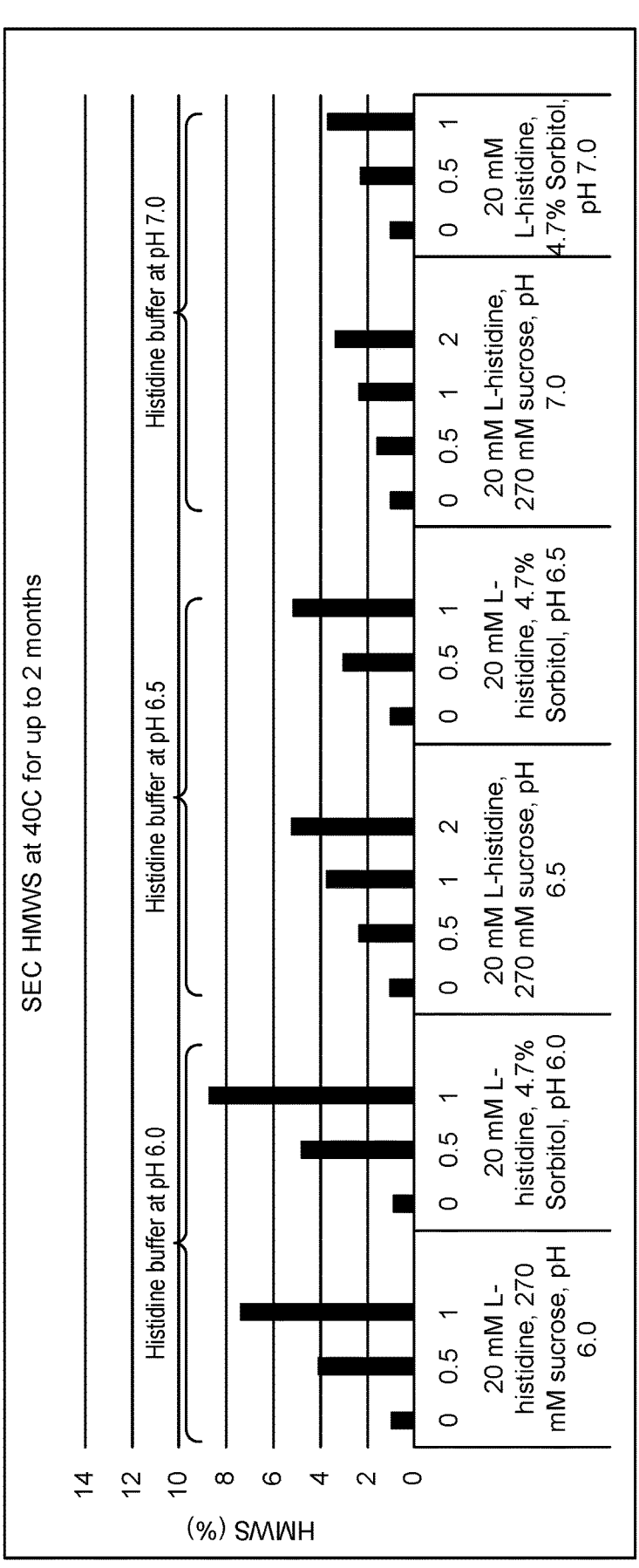
FIG. 9 shows the effect of sucrose and sorbitol on aggregate formation in 10 mg/ml hCD80-Fc at 40° C. as determined by SE-HPLC. (See Example 6.)

All samples remained clear and colorless with no particles observed for the duration of the study. SE-HPLC results shown in FIG. 8 reveal that hCD80-Fc aggregates formed at faster rates in the formulations containing arginine or NaCl compared to corresponding formulations containing sucrose at pH 5.5, 6.5, and 7.0. Sorbitol containing formulations also showed more aggregates than sucrose containing formulations in the histidine buffers at pH 6.0-7.0 (FIG. 9). All formulations had a similar amount of fragments as determined by SE-HPLC analysis. For the preferred pH range of 6.5-7.0, which was determined by pH studies, sucrose provided the best stability for hCD80-Fc among all the excipients evaluated. Sorbitol also provided a better stability profile than arginine and NaCl.

Collectively, the results of pH, buffer species, and excipient selection studies indicate that the hCD80-Fc was most stable in 20 mM L-histidine, 270 mM sucrose, 0.05% PS20 formulation at a pH between 6.5 and 7.0. Because the side chain pKa of L-histidine is 6.0, minimal buffer capacity is expected for L-histidine beyond pH 7.0. Therefore, the formulation of 20 mM L-histidine, 270 mM sucrose, 0.05% PS20 at pH 6.7±0.3 was selected as having desirable properties. A second formulation containing sorbitol instead of sucrose is also selected.

Figure 10:
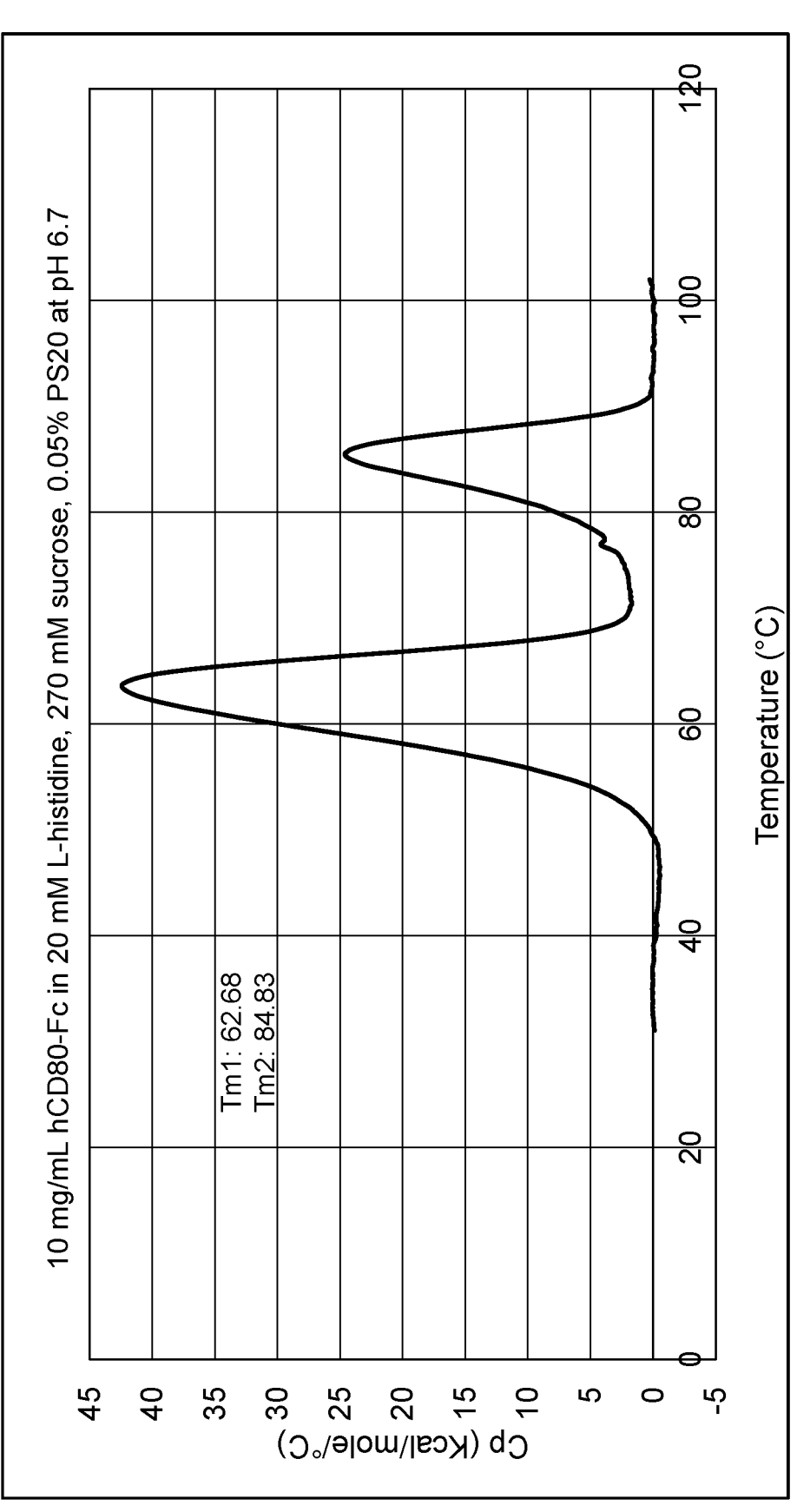
FIG. 10 shows the Differential Scanning calorimetry (DSC) profile of 10 mg/ml hCD80-Fc in 20 mM L-histidine, 270 mM sucrose, 0.05% PS20 at pH 6.7. (See Example 6.)

A Differential Scanning calorimetry (DSC) profile of hCD80-Fc in 20 mM L-histidine, 270 mM sucrose, 0.05% PS20 at pH 6.7 was collected and shown in FIG. 10. Two peaks were observed, with the Tm1=62.7° C. and Tm2=84.8° C.

Example 7: Freeze-thaw Stability of hCD8-Fc

A freeze/thaw study was performed by freezing hCD80-Fc bulk drug substance formulated as 10 mg/mL protein in 20 mM L-histidine, 270 mM sucrose, 0.05% PS20 at pH 6.7 at 500 mL scale at −70° C. and thawing at ambient temperature through 5 cycles. No apparent change in appearance, soluble aggregates, or subvisible particulate matter was detected in the formulation (Table 9).

TABLE 9

Stability of hCD80-Fc Formulation After Freeze-Thaw (FT)

| Cycle Times | Temperature (° C.) | Appearance | | SEC | | | Sub Visible Particulate Matter (cumulative count/mL) | | | |
|---|---|---|---|---|---|---|---|---|---|---|
| | | Clarity | Color | % HMW | % Main | % LMW | ≥2 μm | ≥5 μm | ≥10 μm | ≥25 μm |
| 0FT | Frozen | clear | colorless | 0.1 | 99.9 | 0 | 14 | 7 | 2 | 0 |
| 1FT | −70 C. | clear | colorless | 0.1 | 99.9 | 0 | 12 | 6 | 1 | 0 |
| 2FT | and thawed | clear | colorless | 0.1 | 99.9 | 0 | 9 | 2 | 0 | 0 |
| 3FT | at room | clear | colorless | 0.1 | 99.9 | 0 | 11 | 6 | 1 | 0 |
| 4FT | temperature | clear | colorless | 0.0 | 100.0 | 0 | 16 | 4 | 0 | 0 |
| 5FT | | clear | colorless | 0.0 | 100.0 | 0 | 16 | 6 | 1 | 0 |

Example 8: Agitation Stability of hCD80-Fc

Agitation stress was exerted on the hCD80-Fc by filling hCD80-Fc drug substance into 3 cc glass vials, placing sample vials horizontally on an orbital shaker, and shaking samples at 300 RPM for 72 hours at room temperature (20±5° C.). hCD80-Fc was formulated as 10 mg/mL protein in 20 mM L-histidine, 270 mM sucrose, 0.05% PS20 at pH 6.7. No apparent changes in appearance, soluble aggregates, charge variant, or subvisible particulate matter were detected in the hCD80-Fc formulation samples (Table 10).

TABLE 10

Stability of hCD80-Fc Formulation After Agitation for 72 Hours

| Time Points | Condition | SEC | | | iCIEF | | | Subvisible Particulate Matter (cumulative count /1.6 mL vail) | | | |
|---|---|---|---|---|---|---|---|---|---|---|---|
| | | % HMW | % Main | % LMW | % Acidic | % Main | % Basic | ≥2 μm | ≥5 μm | ≥10 μm | ≥25 μm |
| 0 | Control | 0 | 100 | 0 | 20.2 | 53.6 | 26.2 | 276 | 71 | 30 | 2 |
| T24 h | Control | 0 | 100 | 0 | 20.8 | 53.3 | 25.9 | 252 | 62 | 16 | 0 |
| | Stressed | 0 | 100 | 0 | 21.2 | 52.5 | 26.3 | 117 | 37 | 14 | 0 |
| T48 h | Control | 0 | 100 | 0 | 20.7 | 53.6 | 25.7 | 208 | 64 | 23 | 5 |
| | Stressed | 0.1 | 99.9 | 0 | 21.3 | 53.4 | 26.2 | 197 | 62 | 25 | 2 |
| T72 h | Control | 0 | 100 | 0 | 21.9 | 53.4 | 24.7 | 100 | 37 | 12 | 4 |
| | Stressed | 0 | 100 | 0 | 19.9 | 53.7 | 26.4 | 320 | 89 | 36 | 5 |

Example 9: Confirmation Stability Studies

A 12-month stability study was initiated to evaluate the stability of hCD80-Fc in the first formulation containing 10 mg/mL protein in 20 mM L-histidine, 270 mM sucrose, 0.05% PS20 at pH 6.7 and in the second formulation containing 10 mg/mL protein in 20 mM L-histidine, 270 mM sorbitol, 0.05% PS20 at pH 6.7. The formulated solutions (1.5 ml) were filled into 3 cc type 1 glass vials with 13 mm neck, capped with 13 mm West 4023/50 gray bromobutyl serum stopper, and sealed with aluminum seal. The compatibility of the container closure system with hCD80-Fc was evaluated by placing the vials in inverted positions. Storage conditions at 5° C., 25° C., and 40° C. were used for the stability study and 12 months of stability data were collected. Stability data are shown in Table 11 to Table 13 for the first formulation. Stability data are shown in Table 14 to Table 16 for the backup formulation.

TABLE 11

| Stability of hCD80-Fc Drug Product in the First Formulation at 2-8° C. | | | | | | | | | |
|---|---|---|---|---|---|---|---|---|---|
| | | | 2-8° C. | | | | | | |
| Assay | Acceptance Criteria | T0 | 1 Mon. | 2 Mons. | 3 Mons. | 6 Mons. | 9 Mons. | 12 Mons. |
| Visual Appearance | Clear to opalescent, colorless to slightly yellow, may contain a few proteinaceous particles | Complies | Complies | Complies | Complies | Complies | Complies | Complies |
| pH | 6.4-7.0 | 6.8 | 6.8 | 6.9 | 6.9 | 6.8 | 6.8 | 6.7 |
| Osmolality | 270-370 mOSm/kg | 321 | 312 | 310 | 316 | 304 | 321 | 314 |
| Concentration | 9-11 mg/mL | 11 | 11 | 10 | 11 | 10 | 10 | 11 |
| iCIEF (FIO) | Report % Acidic peaks | 25.3 | 29.9 | 27.4 | 26.7 | 25.2 | 38.5 | 40.3 |
| | Report % Main peaks | 54.3 | 51.5 | 53.2 | 52.9 | 54.7 | 41.2 | 39.1 |
| | Report % Basic peaks | 20.4 | 18.6 | 19.3 | 20.3 | 20.1 | 20.3 | 20.6 |
| SE-HPLC | ≤5.0% Aggregate | 1.0 | 0.8 | 0.8 | 0.8 | 0.3 | 0.7 | 0.7 |
| | ≥90.0% Monomer | 98.9 | 99.0 | 99.2 | 99.2 | 99.7 | 99.3 | 99.3 |
| | Report % Low molecular weight | 0.2 | 0.2 | 0 | 0 | 0 | 0 | 0 |
| CE-SDS Reduced | ≥90.0% Heavy chain and light chain | 99.6 | 99.6 | 99.5 | 99.5 | 99.5 | 99.0 | 99.3 |
| CE-SDS Non-Reduced | Report value (% Main peak) | 99.3 | 98.6 | 98.7 | 99.0 | 99.4 | 99.9 | 98.2 |
| CTLA4 Binding ELISA | 50-150% of Reference Material | 104 | NP | NP | 101 | 105 | NP | 107 |
| CD28 Cell-based Bioassay | Report result (% Reference Material) | 96 | NP | NP | NP | 94 | NP | 107 |
| Subvisible Particulate Matter | ≥10 μm: ≤6000 particles/vial | ≥10 μm: 5 | NP | NP | NP | ≥10 μm: 2 | NP | ≥10 μm: 23 |
| | ≥25 μm: ≤600 particles/vial | ≥25 μm: 2 | | | | ≥25 μm: 2 | | ≥25 μm: 0 |
| | Report number of particles/vial ≥5 μm and ≥2 μm | ≥2 μm: 55 ≥5 μm: 15 | | | | ≥2 μm: 32 ≥5 μm: 6 | | ≥2 μm: 308 ≥5 μm: 93 |

Abbreviations: Mon(s). = Month(s); NP = Not planned; T0 = Time zero.

TABLE 13

| Stability of hCD80-Fc Drug Product in the First Formulation at 25° C. | | | | | | |
|---|---|---|---|---|---|---|
| | | | 25° C. | | | |
| Assay | Acceptance Criteria | T0 | 1 Month | 2 Months | 3 Months | 6 Months |
| Visual Appearance | Clear to opalescent, colorless to slightly yellow, may contain a few proteinaceous particles | Complies | Complies | Complies | Complies | Complies |
| pH | 6.4-7.0 | 6.8 | 6.8 | 6.9 | 6.8 | 6.8 |
| Osmolality | 270-370 mOSm/kg | 321 | 317 | 311 | 317 | 307 |
| Concentration | 9-11 mg/mL | 11 | 11 | 10 | 11 | 10 |
| iCIEF (FIO) | Report % Acidic peaks | 25.3 | 30.5 | 28.1 | 28.0 | 24.9 |
| | Report % Main peaks | 54.3 | 52.5 | 52.1 | 54.6 | 51.9 |
| | Report % Basic peaks | 20.4 | 17.0 | 19.8 | 17.4 | 23.3 |
| SE-HPLC | ≤5.0% Aggregate | 1.0 | 0.7 | 0.7 | 0.7 | 0.3 |
| | ≥90.0% Monomer | 98.9 | 99.1 | 98.9 | 98.6 | 99.7 |
| | Report % Low molecular weight | 0.2 | 0.2 | 0.4 | 0.7 | 0 |
| CE-SDS Reduced | ≥90.0% Heavy chain and light chain | 99.6 | 99.4 | 99.1 | 98.9 | 99.0 |
| CE-SDS Non-Reduced | Report value (% Main peak) | 99.3 | 98.7 | 98.2 | 98.0 | 97.8 |
| CTLA4 Binding ELISA | 50-150% of Reference Material | 104 | NP | NP | 95 | 91 |
| CD28 Cell-based Bioassay | Report result (% Reference Material) | 96 | NP | NP | NP | 61 |
| Subvisible Particulate | ≥10 μm: ≤6000 particles/vial | ≥10 μm: 5 | NP | NP | NP | ≥10 μm: 5 |

TABLE 13-continued

Stability of hCD80-Fc Drug Product in the First Formulation at 25° C.

| | | | 25° C. | | | |
|---|---|---|---|---|---|---|
| Assay | Acceptance Criteria | T0 | 1 Month | 2 Months | 3 Months | 6 Months |
| Matter | ≥25 μm: ≤600 particles/vial | ≥25 μm: 2 | | | | ≥25 μm: 0 |
| | Report number of particles/vial ≥5 μm and ≥2 μm | ≥2 μm: 55 ≥5 μm: 15 | | | | ≥2 μm: 135 ≥5 μm: 35 |

Abbreviations: NP = Not planned; NT = Not tested; T0 = Time zero.

TABLE 13

Stability of hCD80-Fc Drug Product in the First Formulation at 40° C.

| | | | 40° C. | | |
|---|---|---|---|---|---|
| Assay | Acceptance Criteria | T0 | 2 Weeks | 1 Month | 2 Months |
| Visual Appearance | Clear to opalescent, colorless to slightly yellow, may contain a few proteinaceous particles | Complies | Complies | Complies | Complies |
| pH | 6.4-7.0 | 6.8 | 6.8 | 6.9 | 6.9 |
| Osmolality | 270-370 mOSm/kg | 321 | 318 | 317 | 308 |
| Concentration | 9-11 mg/mL | 11 | 11 | 11 | 10 |
| iCIEF (FIO) | Report % Acidic peaks | 25.3 | 24.5 | 25.2 | 25.8 |
| | Report % Main peaks | 54.3 | 53.9 | 55.3 | 53.5 |
| | Report % Basic peaks | 20.4 | 21.5 | 19.5 | 20.6 |
| SE-HPLC | ≤5.0% Aggregate | 1.0 | 0.9 | 1.1 | 1.8 |
| | ≥90.0% Monomer | 98.9 | 98.4 | 97.6 | 96.4 |
| | Report % Low molecular weight | 0.2 | 0.7 | 1.2 | 1.8 |
| CE-SDS Reduced | ≥90.0% Heavy chain and light chain | 99.6 | 98.9 | 98.2 | 96.8 |
| CE-SDS Non-Reduced | Report value (% Main peak) | 99.3 | 97.7 | 96.0 | 93.7 |
| CTLA4 Binding ELISA | 50-150% of Reference Material | 104 | NP | NP | 64 |
| Potency by CD28 Cell-based Bioassay | Report result (% Reference Material) | 96 | NP | NP | 79 |
| Subvisible Particulate Matter | ≥10 μm: ≤6000 particles/vial ≥25 μm: ≤600 particles/vial Report number of particles/vial ≥5 μm and ≥2 μm | ≥10 μm: 5 ≥25 μm: 2 ≥2 μm: 55 ≥5 μm: 15 | NP | NP | ≥10 μm: 5 ≥25 μm: 0 ≥2 μm: 135 ≥5 μm: 35 |

Abbreviations: NP = Not planned;
NT = Not tested;
T0 = Time zero.

TABLE 14

Stability of hCD80-Fc Drug Product in the First Formulation at 2-8° C.

| | | | 2-8° C. | | | | | |
|---|---|---|---|---|---|---|---|---|
| Assay | Acceptance Criteria | T0 | 1 Mon. | 2 Mons. | 3 Mons. | 6 Mons. | 9 Mons. | 12 Mons. |
| Visual Appearance | Clear to opalescent, colorless to slightly yellow, may contain a few proteinaceous particles | Complies | Complies | Complies | Complies | Complies | Complies | Complies |
| pH | 6.4-7.0 | 6.6 | 6.6 | 6.6 | 6.6 | 6.6 | 6.6 | 6.7 |
| Osmolality | 270-370 mOSm/kg | 320 | 312 | 304 | 310 | 300 | 316 | 304 |
| Concentration | 9-11 mg/mL | 10 | 10 | 10 | 10 | 10 | 10 | 10 |

TABLE 14-continued

Stability of hCD80-Fc Drug Product in the First Formulation at 2-8° C.

| | | | 2-8° C. | | | | | |
| Assay | Acceptance Criteria | T0 | 1 Mon. | 2 Mons. | 3 Mons. | 6 Mons. | 9 Mons. | 12 Mons. |
| --- | --- | --- | --- | --- | --- | --- | --- | --- |
| iCIEF (FIO) | Report % Acidic peaks | 24.4 | 29.2 | 25.6 | 25.7 | 25.8 | 37.6 | 27.3 |
| | Report % Main peaks | 53.7 | 53.0 | 55.0 | 54.5 | 54.6 | 43.8 | 55.2 |
| | Report % Basic peaks | 22.0 | 17.8 | 19.3 | 19.9 | 19.6 | 18.6 | 17.5 |
| SE-HPLC | ≤5.0% Aggregate | 1.0 | 0.8 | 0.8 | 0.8 | 0.3 | 0.8 | 0.7 |
| | ≥90.0% Monomer | 98.8 | 99.0 | 99.2 | 99.2 | 99.7 | 99.2 | 99.3 |
| | Report % Low molecular weight | 0.2 | 0.2 | 0 | 0 | 0 | 0 | 0 |
| CE-SDS Reduced | ≥90.0% Heavy chain and light chain | 99.6 | 99.5 | 99.4 | 99.5 | 99.5 | 99.4 | 99.2 |
| CE-SDS Non-Reduced | Report value (% Main peak) | 98.5 | 98.6 | 98.5 | 99.0 | 99.7 | 99.9 | 98.3 |
| CTLA4 Binding ELISA | 50-150% of Reference Material | 99 | NP | NP | 100 | 110 | NP | 101 |
| CD28 Cell-based Bioassay | Report result (% Reference Material) | 91 | NP | NP | NP | 97 | NP | 97 |
| Subvisible Particulate Matter | ≥10 μm: ≤6000 particles/vial | ≥10 μm: 17 | NP | NP | NP | ≥10 μm: 8 | NP | ≥10 μm: 49 |
| | ≥25 μm: ≤600 particles/vial | ≥25 μm: 0 | | | | ≥25 μm: 0 | | ≥25 μm: 15 |
| | Report number of particles/vial ≥5 μm and ≥2 μm | ≥2 μm: 150 ≥5 μm: 42 | | | | ≥2 μm: 38 ≥5 μm: 17 | | ≥2 μm: 222 ≥5 μm: 87 |

Abbreviations: Mon(s). = Month(s); NP = Not planned; T0 = Time zero.

TABLE 15

Stability of hCD80-Fc Drug Product in the First Formulation at 25° C.

| | | | 25° C. | | | |
| Assay | Acceptance Criteria | T0 | 1 Month | 2 Months | 3 Months | 6 Months |
| --- | --- | --- | --- | --- | --- | --- |
| Visual Appearance | Clear to opalescent, colorless to slightly yellow, may contain a few proteinaceous particles | Complies | Complies | Complies | Complies | Complies |
| pH | 6.4-7.0 | 6.6 | 6.6 | 6.6 | 6.6 | 6.6 |
| Osmolality | 270-370 mOsm/kg | 320 | 311 | 304 | 309 | 298 |
| Concentration | 9-11 mg/mL | 10 | 10 | 10 | 10 | 10 |
| iCIEF (FIO) | Report % Acidic peaks | 24.4 | 28.6 | 26.7 | 22.9 | 25.0 |
| | Report % Main peaks | 53.7 | 54.1 | 54.4 | 56.4 | 53.5 |
| | Report % Basic peaks | 22.0 | 17.2 | 18.9 | 20.7 | 21.4 |
| SE-HPLC | ≤5.0% Aggregate | 1.0 | 0.9 | 0.8 | 0.8 | 0.3 |
| | ≥90.0% Monomer | 98.8 | 98.9 | 98.8 | 98.5 | 99.7 |
| | Report % Low molecular weight | 0.2 | 0.2 | 0.4 | 0.7 | 0 |
| CE-SDS Reduced | ≥90.0% Heavy chain and light chain | 99.6 | 99.5 | 98.9 | 98.7 | 98.7 |
| CE-SDS Non-Reduced | Report value (% Main peak) | 98.5 | 98.4 | 98.5 | 98.1 | 97.3 |
| CTLA4 Binding ELISA | 50-150% of Reference Material | 99 | NP | NP | 93 | 86 |
| CD28 Cell-based Bioassay | Report result (% Reference Material) | 91 | NP | NP | NP | 66 |
| Subvisible Particulate Matter | ≥10 μm: ≤6000 particles/vial | ≥10 μm: 17 | NP | NP | NP | ≥10 μm: 3 |
| | ≥25 μm: ≤600 particles/vial | ≥25 μm: 0 | | | | ≥25 μm: 0 |
| | Report number of particles/vial ≥5 μm and ≥ 2μm | ≥2 μm: 150 ≥5 μm: 42 | | | | ≥2 μm: 129 ≥5 μm: 29 |

Abbreviations: NP = Not planned; T0 = Time zero.

TABLE 16

Stability of hCD80-Fc Drug Product in the Second Formulation at 40° C.

| Assay | Acceptance Criteria | T0 | 40° C. 2 Weeks | 1 Month | 2 Months |
|---|---|---|---|---|---|
| Visual Appearance | Clear to opalescent, colorless to slightly yellow, may contain a few proteinaceous particles | Complies | Complies | Complies | Complies |
| pH | 6.4 - 7.0 | 6.6 | 6.6 | 6.6 | 6.6 |
| Osmolality | 270 - 370 mOSm/kg | 320 | 317 | 310 | 307 |
| Concentration | 9 - 11 mg/mL | 10 | 10 | 10 | 10 |
| iCIEF | Report % Acidic peaks | 24.4 | 26.4 | 26.2 | 28.5 |
| | Report % Main peaks | 53.7 | 54.8 | 54.3 | 52.6 |
| | Report % Basic peaks | 22.0 | 18.7 | 19.5 | 19.0 |
| SE-HPLC | ≤5.0% Aggregate | 1.0 | 1.2 | 1.8 | 3.1 |
| | ≥90.0% Monomer | 98.8 | 98.1 | 97.0 | 95.1 |
| | Report % Low molecular weight | 0.2 | 0.7 | 1.3 | 1.8 |
| CE-SDS Reduced | ≥90.0% Heavy chain and light chain | 99.6 | 99.1 | 98.2 | 95.9 |
| CE-SDS Non-Reduced | Report value (% Main peak) | 98.5 | 97.7 | 96.0 | 93.5 |
| CTLA4 Binding ELISA | 50-150% of Reference Material | 99 | NP | NP | 66 |
| Potency by CD28 Cell-based Bioassay | Report result (% Reference Material) | 91 | NP | NP | 78 |
| Subvisible Particulate Matter | ≥10 μm: ≤6000 particles/vial ≥25 μm: ≤600 particles/vial Report number of particles/vial ≥5 μm and ≥2 μm | ≥10 μm: 17 ≥25 μm: 0 ≥2 μm: 150 ≥5 μm: 42 | NP | NP | ≥10 μm: 13 ≥25 μm: 3 ≥2 μm: 325 ≥5 μm: 63 |

Abbreviations: NP = Not planned;
T0 = Time zero.

Stability data of hCD80-Fc drug product under the long-term storage condition of 2-8° C. were collected in real-time in first and second formulations for 12 months. All stability data met the acceptance criteria (Table 11 and Table 14). No clear trend of stability changes was observed in the attributes tested. The results demonstrate that the hCD80-Fc drug product is stable in both formulations under the long-term storage condition for at least 12 months.

Stability data of hCD80-Fc drug product at the accelerated condition of 25° C. were collected for the first and second formulations for 6 months. Overall, storage at the accelerated condition for 6 months resulted in a slight decrease of purity determined by reduced and non-reduced CE-SDS and a slight decrease of potency in CTLA4-binding ELISA and a CD28 cell-based bioassay. No clear change in other product attributes was observed. All stability data are within the acceptance criteria.

Stability data of hCD80-Fc drug product at the stressed condition of 40° C. was collected for 2 months. Some changes were more noticeable in data collected over time. The trends were similar to those shown at the accelerated storage condition at 25° C. An increase of aggregates and fragments with a decrease of monomers was observed by SE-HPLC. In addition, the purity decreased under this condition as demonstrated by reduced and non-reduced CE-SDS analysis. A decrease of potency in the CD28 cell-based bioassay was also observed. These results are consistent with changes expected for protein therapeutics stored under this condition.

The studies in the above Examples were conducted to identify formulation conditions that provide maximal sta-bility for hCD80-Fc. These include pH screening, buffer species selection, and excipient selection studies. hCD80-Fc was most stable in the range of pH 6.5-7.0 in the histidine buffer. hCD80-Fc was also stable when sucrose was used as excipient. A first formulation of 10 mg/mL protein in 20 mM L-histidine, 270 mM sucrose, 0.05% polysorbate 20, pH 6.7 was selected. A second formulation as 10 mg/mL protein in 20 mM L-histidine, 270 mM sorbitol, 0.05% polysorbate 20, pH 6.7 was also selected.

hCD80-Fc was stable in the first formulation under freeze-thaw and agitation conditions. hCD80-Fc in first formulation is expected to be stable both as drug substance when stored at −70° C. and as drug product when stored at 2-8° C. for at least 12 months.

The invention is not to be limited in scope by the specific embodiments described herein. Indeed, various modifications provided herein in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entirety and for all purposes to the same extent as if each individual reference (e.g., publication or patent or patent application) was specifically and individually indicated to be incorporated by reference in its entirety for all purposes.

Other embodiments are within the following claims.

Table of Sequences

The table below provides a listing of certain sequences referenced herein.

| SEQ. ID. NO. | Description | Sequence |
|---|---|---|
| 1 | Human CD80 ECD sequence (without signal sequence) | VIHVTKEVKEVATLSCGHNVSVEELAQTRI YWQKEKKMVLTMMSGDMNIWPEYKNRTIFD ITNNLSIVILALRPSDEGTYECVVLKYEKD AFKREHLAEVTLSVKADFPTPSISDFEIPT SNIRRIICSTSGGFPEPHLSWLENGEELNA INTTVSQDPETELYAVSSKLDFNMTTNHSF MCLIKYGHLRVNQTFNWNTTKQEHFPDN |
| 2 | Mouse CD80 ECD sequence (without signal sequence) | VDEQLSKSVKDKVLLPCRYNSPHEDESEDR IYWQKHDKVVLSVIAGKLKVWPEYKNRTLY DNTTYSLIILGLVLSDRGTYSCVVQKKERG TYEVKHLALVKLSIKADFSTPNITESGNPS ADTKRITCFASGGFPKPRFSWLENGRELPG INTTISQDPESELYTISSQLDFNTTRNHTI KCLIKYGDAHVSEDFTWEKPPEDPPDSKN |
| 3 | Fc human IgG1 | EPKSSDKTHTCPPCPAPELLGGPSVFLFPP KPKDTLMISRTPEVTCVVVDVSHEDPEVKF NWYVDGVEVHNAKTKPREEQYNSTYRVVSV LTVLHQDWLNGKEYKCKVSNKALPAPIEKT ISKAKGQPREPQVYTLPPSRDELTKNQVSL TCLVKGFYPSDIAVEWESNGQPENNYKTTP PVLDSDGSFFLYSKLTVDKSRWQQGNVFSC SVMHEALHNHYTQKSLSLSPGK |

-continued

| SEQ. ID. NO. | Description | Sequence |
|---|---|---|
| 4 | Mouse CD80 ECD mouse Fc IgG2a (Fc portion underlined) | VDEQLSKSVKDKVLLPCRYNSPHEDESEDR IYWQKHDKVVLSVIAGKLKVWPEYKNRTLY DNTTYSLIILGLVLSDRGTYSCVVQKKERG TYEVKHLALVKLSIKADFSTPNITESGNPS ADTKRITCFASGGFPKPRFSWLENGRELPG INTTISQDPESELYTISSQLDFNTTRNHTI KCLIKYGDAHVSEDFTWEKPPEDPPDSKNE PRGPTIKPCPPCKCPAPNLLGGPSVFIFPP KIKDVLMISLSPIVTCVVVDVSEDDPDVQI SWFVNNVEVHTAQTQTHREDYNSTLRVVSA LPIQHQDWMSGKEFKCKVNNKDLPAPIERT ISKPKGSVRAPQVYVLPPPEEEMTKKQVTL TCMVTDFMPEDIYVEWTNNGKTELNYKNTE PVLDSDGSYFMYSKLRVEKKNWVERNSYSC SVVHEGLHNHHTTKSFSRTPGK |
| 5 | Human CD80 ECD Human Fc IgG1 WT (Fc portion underlined) | VIHVTKEVKEVATLSCGHNVSVEELAQTRI YWQKEKKMVLTMMSGDMNIWPEYKNRTIFD ITNNLSIVILALRPSDEGTYECVVLKYEKD AFKREHLAEVTLSVKADFPTPSISDFEIPT SNIRRIICSTSGGFPEPHLSWLENGEELNA INTTVSQDPETELYAVSSKLDFNMTTNHSF MCLIKYGHLRVNQTFNWNTTKQEHFPDNEP KSSDKTHTCPPCPAPELLGGPSVFLFPPKP KDTLMISRTPEVTCVVVDVSHEDPEVKFNW YVDGVEVHNAKTKPREEQYNSTYRVVSVLT VLHQDWLNGKEYKCKVSNKALPAPIEKTIS KAKGQPREPQVYTLPPSRDELTKNQVSLTC LVKGFYPSDIAVEWESNGQPENNYKTTPPV LDSDGSFFLYSKLTVDKSRWQQGNVFSCSV MHEALHNHYTQKSLSLSPGK |

What is claimed:

1. A pharmaceutical composition consisting of (i) sialy-lated CD80 ECD-Fc fusion molecules, (ii) about 20 mM L-histidine, (iii) about 270 mM sucrose, and (iv) about 0.05% weight/volume polysorbate 20, wherein the pH of the composition is about 6.7.

2. A pharmaceutical composition consisting of (i) sialy-lated CD80 ECD-Fc fusion molecules, (ii) about 20 mM L-histidine, (iii) about 270 mM sorbitol, and (iv) about 0.05% weight/volume polysorbate 20, wherein the pH of the composition is about 6.7.

3. A syringe or vial comprising the pharmaceutical composition of claim 1.

4. The pharmaceutical composition of claim 1, wherein the concentration of CD80 ECD-Fc fusion molecules is about 5 mg/ml to about 15 mg/ml.

5. The pharmaceutical composition of claim 4, wherein the concentration of the CD80 ECD-Fc fusion molecules is about 10 mg/ml.

6. The pharmaceutical composition of claim 1, wherein the composition is a liquid.

7. The pharmaceutical composition of claim 1, wherein the composition is for intravenous administration.

8. The pharmaceutical composition of claim 1, wherein the CD80 ECD-Fc fusion molecules comprise a human CD80 ECD and a human IgG1 Fc domain.

9. The pharmaceutical composition of claim 1, wherein the CD80 ECD-Fc fusion molecules comprise 15-60 moles sialic acid (SA) per mole of fusion protein.

10. The pharmaceutical composition of claim 2, wherein the concentration of CD80 ECD-Fc fusion molecules is about 5 mg/ml to about 15 mg/ml.

11. The pharmaceutical composition of claim 10, wherein the concentration of the CD80 ECD-Fc fusion molecules is about 10 mg/ml.

12. The pharmaceutical composition of claim 2, wherein the composition is a liquid.

13. The pharmaceutical composition of claim 2, wherein the composition is for intravenous administration.

14. The pharmaceutical composition of claim 2, wherein the CD80 ECD-Fc fusion molecules comprise a human CD80 ECD and a human IgG1 Fc domain.

15. The pharmaceutical composition of claim 2, wherein the CD80 ECD-Fc fusion molecules comprise 15-60 moles sialic acid (SA) per mole of fusion protein.

16. A syringe or vial comprising the pharmaceutical composition of claim 2.

* * * * *

SEQUENCE LISTING

<160> NUMBER OF SEQ ID NOS: 5

<210> SEQ ID NO 1
<211> LENGTH: 208
<212> TYPE: PRT
<213> ORGANISM: Artificial Sequence
<220> FEATURE:
<223> OTHER INFORMATION: Human CD80 ECD sequence (without signal sequence)

<400> SEQUENCE: 1

```
Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
```

```
      130              135              140

Gly Glu Glu Leu Asn Ala Ile Asn Thr Thr Val Ser Gln Asp Pro Glu
145              150              155              160

Thr Glu Leu Tyr Ala Val Ser Ser Lys Leu Asp Phe Asn Met Thr Thr
                165              170              175

Asn His Ser Phe Met Cys Leu Ile Lys Tyr Gly His Leu Arg Val Asn
                180              185              190

Gln Thr Phe Asn Trp Asn Thr Thr Lys Gln Glu His Phe Pro Asp Asn
            195              200              205
```

<210> SEQ ID NO 2
<211> LENGTH: 209
<212> TYPE: PRT
<213> ORGANISM: Artificial Sequence
<220> FEATURE:
<223> OTHER INFORMATION: Mouse CD80 ECD sequence (without signal
      sequence)

<400> SEQUENCE: 2

```
Val Asp Glu Gln Leu Ser Lys Ser Val Lys Asp Lys Val Leu Leu Pro
1               5               10              15

Cys Arg Tyr Asn Ser Pro His Glu Asp Glu Ser Glu Asp Arg Ile Tyr
            20              25              30

Trp Gln Lys His Asp Lys Val Val Leu Ser Val Ile Ala Gly Lys Leu
        35              40              45

Lys Val Trp Pro Glu Tyr Lys Asn Arg Thr Leu Tyr Asp Asn Thr Thr
    50              55              60

Tyr Ser Leu Ile Ile Leu Gly Leu Val Leu Ser Asp Arg Gly Thr Tyr
65              70              75              80

Ser Cys Val Val Gln Lys Lys Glu Arg Gly Thr Tyr Glu Val Lys His
            85              90              95

Leu Ala Leu Val Lys Leu Ser Ile Lys Ala Asp Phe Ser Thr Pro Asn
            100             105             110

Ile Thr Glu Ser Gly Asn Pro Ser Ala Asp Thr Lys Arg Ile Thr Cys
        115             120             125

Phe Ala Ser Gly Gly Phe Pro Lys Pro Arg Phe Ser Trp Leu Glu Asn
        130             135             140

Gly Arg Glu Leu Pro Gly Ile Asn Thr Thr Ile Ser Gln Asp Pro Glu
145             150             155             160

Ser Glu Leu Tyr Thr Ile Ser Ser Gln Leu Asp Phe Asn Thr Thr Arg
                165             170             175

Asn His Thr Ile Lys Cys Leu Ile Lys Tyr Gly Asp Ala His Val Ser
                180             185             190

Glu Asp Phe Thr Trp Glu Lys Pro Pro Glu Asp Pro Pro Asp Ser Lys
            195             200             205

Asn
```

<210> SEQ ID NO 3
<211> LENGTH: 232
<212> TYPE: PRT
<213> ORGANISM: Artificial Sequence
<220> FEATURE:
<223> OTHER INFORMATION: Fc human IgG1

<400> SEQUENCE: 3

```
Glu Pro Lys Ser Ser Asp Lys Thr His Thr Cys Pro Pro Cys Pro Ala
1               5               10              15
```

-continued

```
Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
            130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
                180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
            210                 215                 220

Ser Leu Ser Leu Ser Pro Gly Lys
225                 230
```

<210> SEQ ID NO 4
<211> LENGTH: 442
<212> TYPE: PRT
<213> ORGANISM: Artificial Sequence
<220> FEATURE:
<223> OTHER INFORMATION: Mouse CD80 ECD mouse Fc IgG2a

<400> SEQUENCE: 4

```
Val Asp Glu Gln Leu Ser Lys Ser Val Lys Asp Lys Val Leu Leu Pro
1                   5                   10                  15

Cys Arg Tyr Asn Ser Pro His Glu Asp Glu Ser Glu Asp Arg Ile Tyr
            20                  25                  30

Trp Gln Lys His Asp Lys Val Val Leu Ser Val Ile Ala Gly Lys Leu
            35                  40                  45

Lys Val Trp Pro Glu Tyr Lys Asn Arg Thr Leu Tyr Asp Asn Thr Thr
    50                  55                  60

Tyr Ser Leu Ile Ile Leu Gly Leu Val Leu Ser Asp Arg Gly Thr Tyr
65                  70                  75                  80

Ser Cys Val Val Gln Lys Lys Glu Arg Gly Thr Tyr Glu Val Lys His
                85                  90                  95

Leu Ala Leu Val Lys Leu Ser Ile Lys Ala Asp Phe Ser Thr Pro Asn
            100                 105                 110

Ile Thr Glu Ser Gly Asn Pro Ser Ala Asp Thr Lys Arg Ile Thr Cys
            115                 120                 125

Phe Ala Ser Gly Gly Phe Pro Lys Pro Arg Phe Ser Trp Leu Glu Asn
            130                 135                 140
```

-continued

```
Gly Arg Glu Leu Pro Gly Ile Asn Thr Thr Ile Ser Gln Asp Pro Glu
145             150             155             160

Ser Glu Leu Tyr Thr Ile Ser Ser Gln Leu Asp Phe Asn Thr Thr Arg
                165             170             175

Asn His Thr Ile Lys Cys Leu Ile Lys Tyr Gly Asp Ala His Val Ser
            180             185             190

Glu Asp Phe Thr Trp Glu Lys Pro Pro Glu Asp Pro Pro Asp Ser Lys
            195             200             205

Asn Glu Pro Arg Gly Pro Thr Ile Lys Pro Cys Pro Pro Cys Lys Cys
    210             215             220

Pro Ala Pro Asn Leu Leu Gly Gly Pro Ser Val Phe Ile Phe Pro Pro
225             230             235             240

Lys Ile Lys Asp Val Leu Met Ile Ser Leu Ser Pro Ile Val Thr Cys
            245             250             255

Val Val Val Asp Val Ser Glu Asp Asp Pro Asp Val Gln Ile Ser Trp
            260             265             270

Phe Val Asn Asn Val Glu Val His Thr Ala Gln Thr Gln Thr His Arg
            275             280             285

Glu Asp Tyr Asn Ser Thr Leu Arg Val Val Ser Ala Leu Pro Ile Gln
    290             295             300

His Gln Asp Trp Met Ser Gly Lys Glu Phe Lys Cys Lys Val Asn Asn
305             310             315             320

Lys Asp Leu Pro Ala Pro Ile Glu Arg Thr Ile Ser Lys Pro Lys Gly
            325             330             335

Ser Val Arg Ala Pro Gln Val Tyr Val Leu Pro Pro Pro Glu Glu Glu
            340             345             350

Met Thr Lys Lys Gln Val Thr Leu Thr Cys Met Val Thr Asp Phe Met
            355             360             365

Pro Glu Asp Ile Tyr Val Glu Trp Thr Asn Asn Gly Lys Thr Glu Leu
    370             375             380

Asn Tyr Lys Asn Thr Glu Pro Val Leu Asp Ser Asp Gly Ser Tyr Phe
385             390             395             400

Met Tyr Ser Lys Leu Arg Val Glu Lys Lys Asn Trp Val Glu Arg Asn
            405             410             415

Ser Tyr Ser Cys Ser Val Val His Glu Gly Leu His Asn His His Thr
            420             425             430

Thr Lys Ser Phe Ser Arg Thr Pro Gly Lys
            435             440
```

```
<210> SEQ ID NO 5
<211> LENGTH: 440
<212> TYPE: PRT
<213> ORGANISM: Artificial Sequence
<220> FEATURE:
<223> OTHER INFORMATION: Human CD80 ECD Human Fc IgG1 WT

<400> SEQUENCE: 5
```

```
Val Ile His Val Thr Lys Glu Val Lys Glu Val Ala Thr Leu Ser Cys
1               5               10              15

Gly His Asn Val Ser Val Glu Glu Leu Ala Gln Thr Arg Ile Tyr Trp
                20              25              30

Gln Lys Glu Lys Lys Met Val Leu Thr Met Met Ser Gly Asp Met Asn
            35              40              45

Ile Trp Pro Glu Tyr Lys Asn Arg Thr Ile Phe Asp Ile Thr Asn Asn
    50              55              60
```

-continued

```
Leu Ser Ile Val Ile Leu Ala Leu Arg Pro Ser Asp Glu Gly Thr Tyr
65              70              75                  80

Glu Cys Val Val Leu Lys Tyr Glu Lys Asp Ala Phe Lys Arg Glu His
                85              90                  95

Leu Ala Glu Val Thr Leu Ser Val Lys Ala Asp Phe Pro Thr Pro Ser
            100             105             110

Ile Ser Asp Phe Glu Ile Pro Thr Ser Asn Ile Arg Arg Ile Ile Cys
            115             120             125

Ser Thr Ser Gly Gly Phe Pro Glu Pro His Leu Ser Trp Leu Glu Asn
        130             135             140

Gly Glu Glu Leu Asn Ala Ile Asn Thr Thr Val Ser Gln Asp Pro Glu
145             150             155             160

Thr Glu Leu Tyr Ala Val Ser Ser Lys Leu Asp Phe Asn Met Thr Thr
            165             170             175

Asn His Ser Phe Met Cys Leu Ile Lys Tyr Gly His Leu Arg Val Asn
            180             185             190

Gln Thr Phe Asn Trp Asn Thr Thr Lys Gln Glu His Phe Pro Asp Asn
        195             200             205

Glu Pro Lys Ser Ser Asp Lys Thr His Thr Cys Pro Pro Cys Pro Ala
    210             215             220

Pro Glu Leu Leu Gly Gly Pro Ser Val Phe Leu Phe Pro Pro Lys Pro
225             230             235             240

Lys Asp Thr Leu Met Ile Ser Arg Thr Pro Glu Val Thr Cys Val Val
            245             250             255

Val Asp Val Ser His Glu Asp Pro Glu Val Lys Phe Asn Trp Tyr Val
            260             265             270

Asp Gly Val Glu Val His Asn Ala Lys Thr Lys Pro Arg Glu Glu Gln
        275             280             285

Tyr Asn Ser Thr Tyr Arg Val Val Ser Val Leu Thr Val Leu His Gln
    290             295             300

Asp Trp Leu Asn Gly Lys Glu Tyr Lys Cys Lys Val Ser Asn Lys Ala
305             310             315             320

Leu Pro Ala Pro Ile Glu Lys Thr Ile Ser Lys Ala Lys Gly Gln Pro
            325             330             335

Arg Glu Pro Gln Val Tyr Thr Leu Pro Pro Ser Arg Asp Glu Leu Thr
            340             345             350

Lys Asn Gln Val Ser Leu Thr Cys Leu Val Lys Gly Phe Tyr Pro Ser
        355             360             365

Asp Ile Ala Val Glu Trp Glu Ser Asn Gly Gln Pro Glu Asn Asn Tyr
    370             375             380

Lys Thr Thr Pro Pro Val Leu Asp Ser Asp Gly Ser Phe Phe Leu Tyr
385             390             395             400

Ser Lys Leu Thr Val Asp Lys Ser Arg Trp Gln Gln Gly Asn Val Phe
            405             410             415

Ser Cys Ser Val Met His Glu Ala Leu His Asn His Tyr Thr Gln Lys
            420             425             430

Ser Leu Ser Leu Ser Pro Gly Lys
            435             440
```